United States Patent [19]
Ahmed

[11] Patent Number: 5,980,865
[45] Date of Patent: Nov. 9, 1999

[54] METHOD FOR TREATING LATE PHASE ALLERGIC REACTIONS AND INFLAMMATORY DISEASES

[75] Inventor: Tahir Ahmed, Coral Gables, Fla.

[73] Assignee: Baker Norton Pharmaceuticals, Inc., Miami, Fla.

[21] Appl. No.: 08/904,565

[22] Filed: Aug. 4, 1997

Related U.S. Application Data

[63] Continuation-in-part of application No. 08/516,786, Aug. 18, 1995, Pat. No. 5,690,910.

[51] Int. Cl.$^6$ ..................................................... A61K 9/12
[52] U.S. Cl. .............................. 424/45; 424/46; 514/56; 514/826; 514/851
[58] Field of Search .................... 424/45, 46; 514/56, 514/826, 851

[56] References Cited

U.S. PATENT DOCUMENTS 5,527,785  6/1996  Bevilacqua et al. .
5,690,910  11/1997  Ahmed et al. .............................. 424/45

FOREIGN PATENT DOCUMENTS

94/18988  9/1994  WIPO .

OTHER PUBLICATIONS

Ahmed et al., *American Physiol. Soc.*, pp. 893–901 (1994).
Ahmed, *Resp. Drug Delivery IV*, pp. 55–63 (1994).
Ahmed et al., *American Physiol. Soc.*, pp. 1492–1498 (1993).
Ahmed et al., *N. Engl. J. Med.*, vol. 329, pp. 90–95 (1993).
Ahmed et. al., *Am. Rev. Respir. Dis.*, vol. 145, pp. 566–570 (1992).
Karnovsky et al., *Airwaves and Vascular Remodelling*, pp. 45–69 (1994).
Ashkin et al., *Am. Rev. Resp. Dis.*, vol. 147, No. 4, p. A660 (1993).
Lucio et al., *American Physiol. Soc.*, pp. 1093–1101 (1992).
Page, *Lancet*, vol. 337, pp. 717–720 (1991).
Lemanske et al., "Late Phase Allergic Reactions" in *Allergies, Principles and Practice*, Mosby Yearbook, Inc., 4th ed. (1997).

*Primary Examiner*—Raj Bawa
*Attorney, Agent, or Firm*—Kirschstein, et. al.

[57] ABSTRACT

A method of treating a mammalian patient suffering from or prone to a condition characterized by late phase allergic reactions, airway hyperresponsiveness or inflammatory reactions, e.g., asthma, allergic rhinitis, allergic dermatitis, allergic conjunctivitis, inflammatory bowel disease or rheumatoid arthritis, comprising the administration to the patient of an oral, parenteral, intrabronchial, topical, intranasal or intraocular pharmaceutical composition containing in each dose about 0.005 to about 1.0 mg per kilogram of patient body weight of ultra-low molecular weight heparins (ULMWH) or other sulfated polysaccharides having average molecular weights of about 1,000–3,000 daltons. Suitable inhalant and other pharmaceutical compositions for use in the novel treatment method are also disclosed.

35 Claims, 28 Drawing Sheets

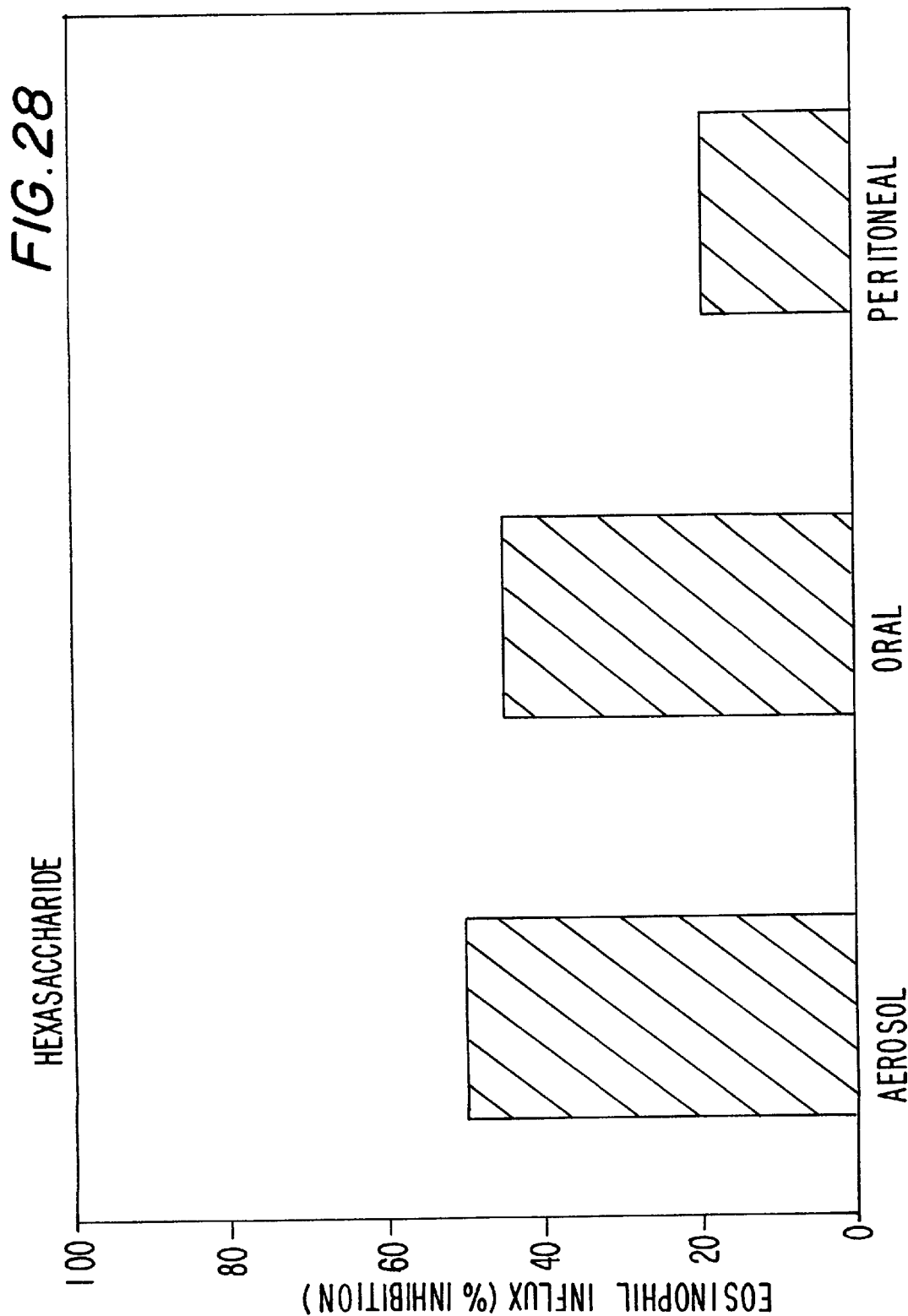

METHOD FOR TREATING LATE PHASE ALLERGIC REACTIONS AND INFLAMMATORY DISEASES

CROSS-REFERENCE TO RELATED APPLICATION

This application is a continuation-in-part of application Ser. No. 08/516,786, filed Aug. 18, 1995, now U.S. Pat. No. 5,690,910 issued Nov. 15, 1997.

REFERENCE TO DISCLOSURE DOCUMENT

This application incorporates material included in Disclosure Document No. 401115, filed in the Patent and Trademark Office on Jun. 5, 1996.

BACKGROUND OF THE INVENTION

1. Field of the Invention

The invention relates to methods and compositions for preventing and reversing the symptoms and manifestations of late phase allergic reactions and inflammatory diseases.

2. Description of the Prior Art

Chronic asthma can be considered to be predominantly an inflammatory disease with associated bronchospasm. The degree of reactivity and narrowing of the bronchi in response to stimuli is greater in asthmatics than in normal individuals. Persistent inflammation is responsible for the bronchial hyperreactivity or airway hyperresponsiveness (AHR). Mucosal edema, mucus plugging and hypersecretion may be present; pulmonary parenchyma is normal. Airway narrowing may reverse spontaneously or with therapy. Type 1 (immediate) immune responses may play an important role in the development of asthma in children and many adults; however, when onset of disease occurs in adulthood, allergic factors may be difficult to identify. Exposure to cold dry air, exercise and other aggravating factors also may trigger asthma.

The general goals of drug therapy for asthma are prevention of bronchospasm and long-term control of bronchial hyperreactivity. Because it is usually not possible for either patient or physician to predict when bronchospasm may occur, patients with all but the most episodic and/or entirely seasonal attacks may require continuous therapy.

Beta agonists are useful as bronchodilator agents; they stimulate $beta_2$-adrenergic receptors, increase intracellular cAMP, and may inhibit the release of mast cell mediators. Other useful drugs include theophylline and related xanthine drugs, which produce bronchodilation through unknown mechanisms; the biscromone, cromolyn, which prevents the release of mediator substances and blocks respiratory neuronal reflexes; and corticosteroids, which primarily decrease inflammation and edema. Anticholinergic drugs may relieve bronchospasm by blocking parasympathetic cholinergic impulses at the receptor level. Antihistamines occasionally prevent or abort allergic asthmatic episodes, particularly in children, but they can only be partially effective in asthma because histamine is only one of many mediators.

The current drug modalities used for treatment of allergy-induced asthma suffer from a number of drawbacks. In general, the conventional agents have a relatively short duration of action and may be partially or wholly ineffective when administered after antigen challenge occurs. Moreover, because of serious adverse effects associated with the use of agents such as $beta_2$-adrenergic agonists and corticosteroids, the therapeutic margin of safety with such agents is relatively narrow and patients using them must be carefully monitored.

Bronchial hyperreactivity (or AHR) is a hallmark of asthma and is closely related to underlying airway inflammation. Worsening of asthma and airway inflammation is associated with increase in bronchial hyperreactivity, which can be induced by both antigenic and non-antigenic stimuli. $Beta_2$-adrenergic agonists are potent agents for the treatment of bronchospasm, but have no effect on airway inflammation or bronchial hyperreactivity. In fact, chronic use of $beta_2$-adrenergic agents alone, by causing down regulation of $beta_2$-receptors, may worsen bronchial hyperreactivity. At present, corticosteroids are the only effective agents available which diminish bronchial hyperreactivity. Although inhaled corticosteroids are relatively safe in adult patients with asthma, these agents have tremendous toxicity in children, including adrenal suppression and reduced bone density and growth. Thus, the search for safer and effective agents which diminish bronchial hyperreactivity continues.

Patients with allergic asthma, following an inhalation challenge with the specific antigen exhibit at least two different patterns of bronchial responses. The majority of subjects develop an acute bronchoconstrictor response only, which resolves spontaneously within 1–3 hours; these subjects are termed "acute responders". A smaller number of subjects, however, develop both an early and a late response. These subjects are termed "dual responders". In dual responders, the acute response, which resolves spontaneously, is followed 4–12 hours later by a secondary increase in airway resistance ("late phase response"). Late responses and thus dual responders are of clinical importance, because of their association with prolonged airway hyperreactivity or hyperresponsiveness (AHR), worsening of symptoms and generally worse form of clinical asthma, requiring aggressive therapy.

Pharmacological studies in allergic animals have demonstrated that not only the bronchoconstrictor response but also the inflammatory cell influx and the mediator release pattern in dual responders is quite different from acute responders. Whereas histamine is the likely bronchoconstrictor mediator during acute phase, activated products of the lipoxygenase pathway (i.e., leukotrienes) may be the major mediator involved in late phase reaction. Mast cells, however, have a central role in IgE-mediated allergic airway responses, and cromolyn sodium (a mast-cell membrane stabilizer), theoretically should prevent bronchoconstrictor responses in both "acute" and "dual" responders. Heterogeneity of mast cell subtypes may play a significant role in divergent responses and it may be dependent upon differences in signal transduction (second messenger system).

It has been discovered in the past several years that heparin administered intrabronchially can be an effective inhibitor of bronchospasm and bronchoconstriction and is consequently of value in the prophylaxis of asthma (see, e.g., Ahmed et al., *New Eng. J. Med.*, 329:90–95,1993; Ahmed, *Resp. Drug Deliv.*, IV:55–63, 1994). It has been discovered further that low molecular weight heparins, e.g., heparins with an average molecular weight of 4,000–5,000 daltons, effectively prevent antigen-induced bronchoconstriction; these low molecular weight heparins also exhibit considerably less anticoagulant activity than commercial heparin, a desirable property when these agents are used in the treatment of asthma (see Ashkin et al., *Am. Rev. Resp. Dis.*, 1993 Intl. Conf. Abstracts, p. A660). Both commercial and low-weight heparins are not effective, however, in suppressing AHR when administered after the patient has been exposed to antigen.

In parent application Ser. No. 08/516,786 we disclosed that ultra-low molecular weight heparins (ULMWH) having an average molecular weight less than about 3,000 daltons are effective in suppressing AHR in acute asthmatic responders, even when administered after the patient has been challenged with antigen. However, experimental and clinical studies have shown that while inhaled commercial heparin can also attenuate early phase antigen-induced bronchoconstriction in acute responders (though not after antigen challenge) it is ineffective in the treatment of dual responders. Hence, there was still considerable doubt after our earlier work with ULMWH as to whether these substances would show efficacy in the treatment of dual or late responders as they do in acute responders.

The current, conventional therapeutic modalities for asthmatic patients who are dual responders are generally a more aggressive and time-prolonged version of the therapies practiced on acute responders, described above. However, these therapies are not particularly effective in suppressing AHR, as noted previously, and, as a result of their generally short duration of action, cannot prevent the late phase reaction and AHR observed in dual responders.

It should be noted, however, that the airways are merely a prototype of organs or tissues affected by late phase reactions (LPR's). It has been established in the medical literature that the late phase bronchoconstriction and AHR observed in dual responder asthmatic patients is not an isolated phenomenon restricted to asthmatic or even pulmonary conditions. There are cutaneous, nasal, ocular and systemic manifestations of LPR's in addition to the pulmonary ones. These allergic LPR phenomena are considered closely interrelated from the point of view of immunologic mechanisms. See Lemanske and Kaliner, "Late Phase Allergic Reactions", published in *Allergies. Principles and Practice* (Mosby Yearbook, Inc., 4th ed. 1997). According to the latest understanding of LPR mechanisms it appears that the clinical diseases (whether of the skin, lung, nose, eye or other organs) recognized to involve allergic mechanisms have a histologic inflammatory component which follows the immediate allergic or hypersensitivity reaction that occurs on antigen challenge. This sequence of response appears to be connected to mast cell mediators and propagated by other resident cells within target organs or by cells recruited into the sites of mast cell or basophilic degranulation. Corticosteroids which have proven valuable in the management of various allergic diseases and asthma may be beneficial because of their ability to attenuate this inflammatory process.

Furthermore, there are extra-pulmonary diseases where inflammatory response plays a major role, for example, inflammatory bowel disease, rheumatoid arthritis, glomerulonephritis and inflammatory skin disease. These conditions are also often treated with anti-inflammatory agents which may be of short duration or which, like steroidal and non-steroidal anti-inflammatory drugs, may frequently cause adverse systemic or gastrointestinal reactions.

Improved pharmaceutical treatments for late phase allergic reactions and inflammatory diseases are required.

SUMMARY OF THE INVENTION

It is an object of this invention to provide more effective and safer methods and compositions for treatment of conditions characterized by late phase allergic reactions or inflammatory reactions.

It is another object of the present invention to provide a method and compositions for treatment of antigen-induced late phase asthma and bronchial hyperreactivity which do not suffer from the drawbacks of the prior art.

It is a further object of the present invention to provide a method and compositions for the treatment of asthmatic dual responders which are effective in preventing and reversing the manifestations of late phase asthma.

Still another object of the present invention is to provide a method and compositions as described above which are highly effective in diminishing specific and non-specific bronchial hyperreactivity, and even when administered after antigen challenge to the patient.

In keeping with these objects and others which will become apparent hereinafter, the invention resides in a method of treating a mammalian patient suffering from a condition which is characterized by late phase allergic reactions, including, e.g., pulmonary, nasal, cutaneous, ocular and systemic LPR's, or which is characterized by inflammatory reactions, through the intrabronchial, oral, topical, parenteral, intranasal or intraocular administration to the patient of a pharmaceutical composition comprising from about 0.005 to about 1.0 mg of ultra-low molecular weight heparins (ULMWH) per kilogram of patient body weight in each dose. The administration of these heparins can be on an acute basis such as following antigen challenge, or on a chronic basis to suppress inflammatory reactions such as bronchial hyperreactivity in asthma patients.

The ULMWH effective in the method of the invention have average molecular weights of about 1,000 to about 3,000 daltons and may exhibit a low level of anticoagulant activity or substantially no anticoagulant activity at all. Novel pharmaceutical compositions are also provided including, e.g., inhalant (intrabronchial) compositions in the form of liquid or powder nebulizer or aerosol compositions containing suitable concentrations of these ULMWH.

+=Significantly different from baseline (P<0.05)

*=Significantly different from dual responders (P<0.05)

FIG. 2 comprises two graphs illustrating the differential effects of inhaled commercial heparin on antigen-induced bronchoconstriction in two groups of allergic sheep, one composed of acute responders (n=8) and the other of dual responders (n=13).

+=Significantly different from baseline (P<0.05)

*=Significantly different from control (P<0.05)

Figure 3:
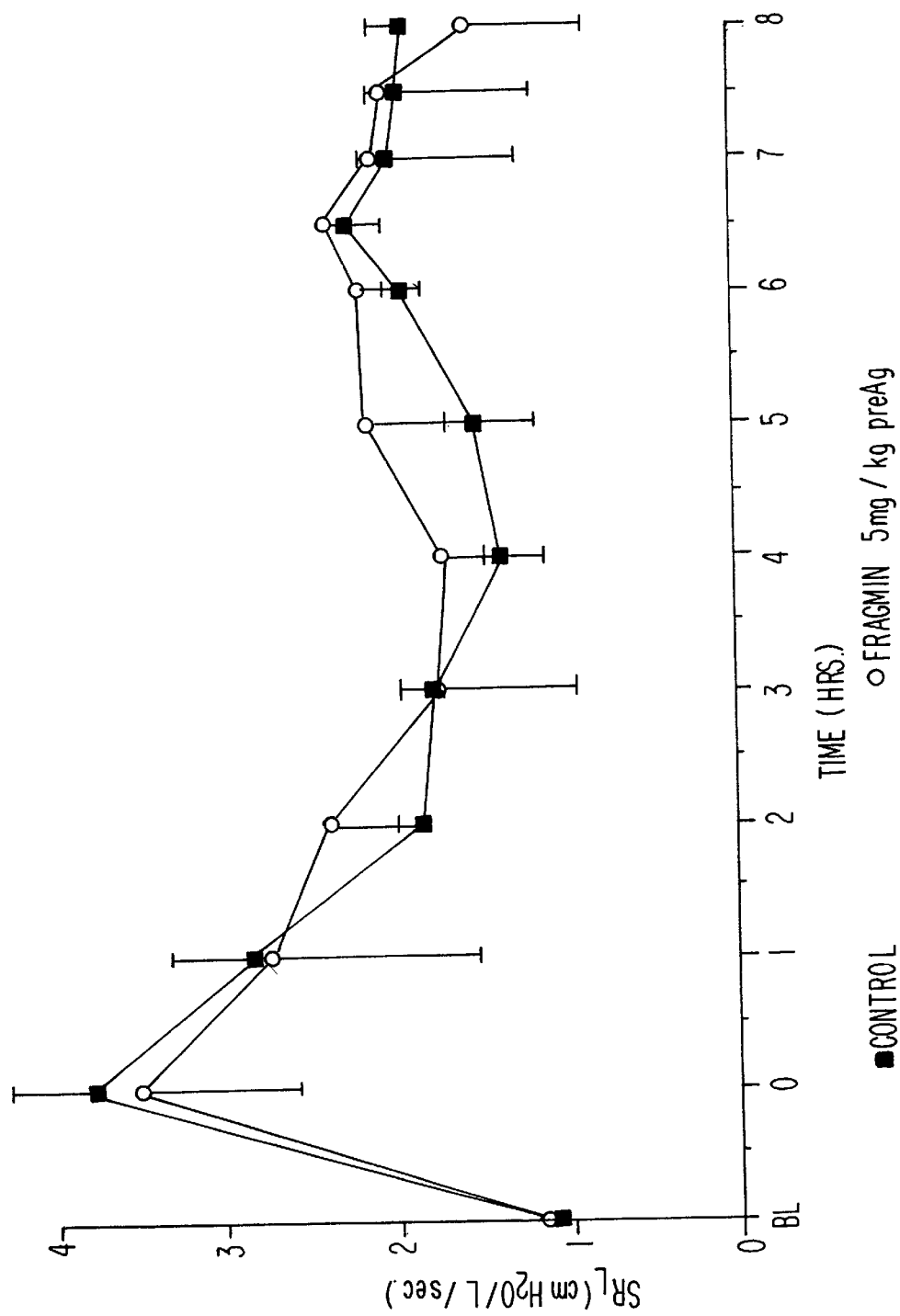

FIG. 3 is a graph illustrating the effect of pretreatment with inhaled Fragmin™ (avg. mol. wt. 5,030 daltons) at 5.0 mg/kg on antigen-induced bronchoconstriction in dual responder allergic sheep. Data are shown as mean $SR_L$ (in cm $H_2O$/L/sec) in a group of animals exposed to antigen, first with no drug treatment and again several days later after pretreatment with Fragmin.

Figure 4:
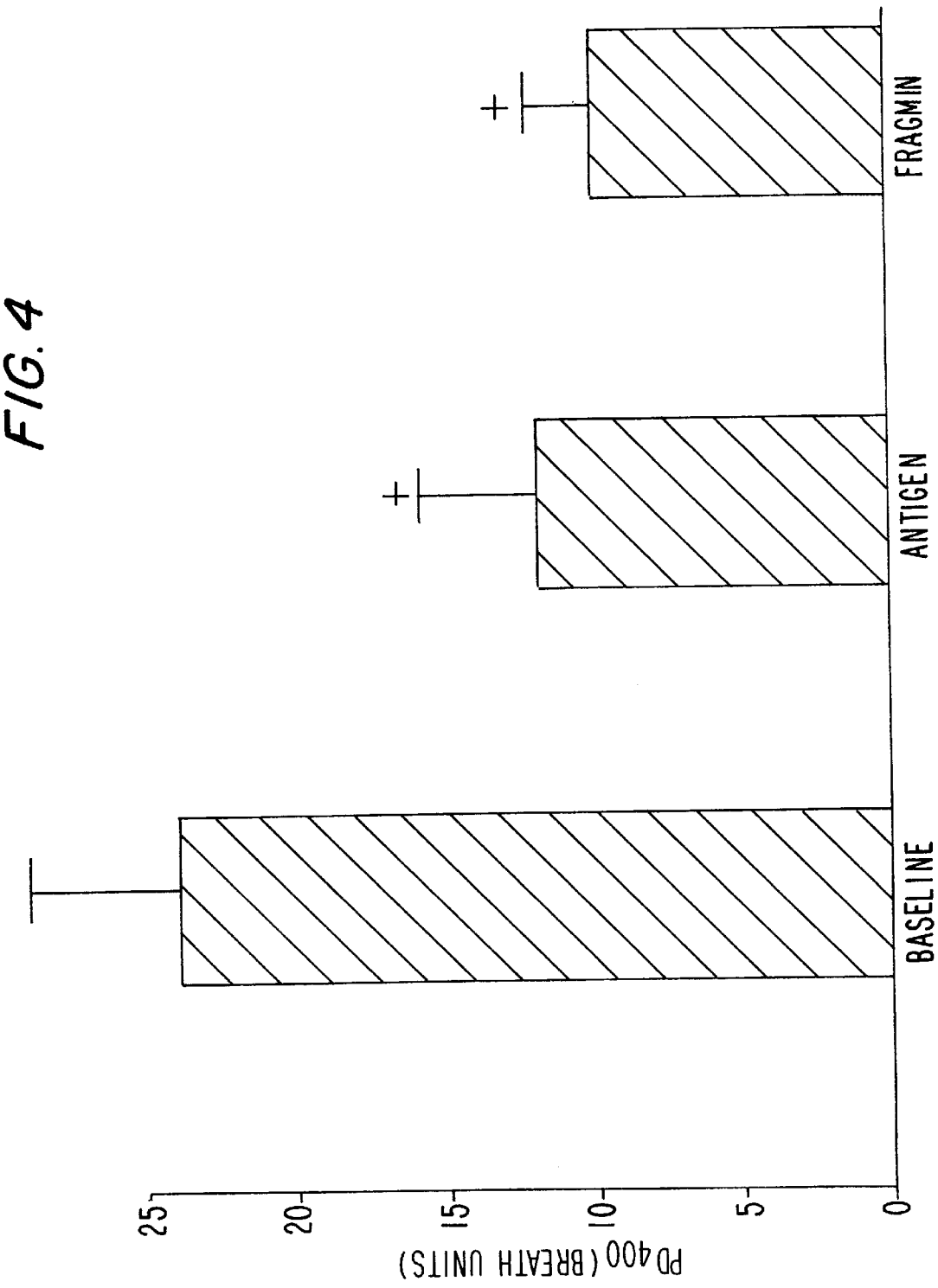

FIG. 4 is a bar graph illustrating the effect of pretreatment with inhaled Fragmin™ at 5.0 mg/kg on AHR in allergic sheep. Data are shown as mean ±SE $PD_{400}$ in breath units at baseline and 24 hours post-antigen challenge in a group of animals exposed to antigen, first with no drug treatment and again several days later after pretreatment with Fragmin.

$PD_{400}$=Cumulative provocating dose of carbachol, increasing $SR_L$ to 400% above baseline +=Significantly different from baseline (P<0.05)

Figure 5:
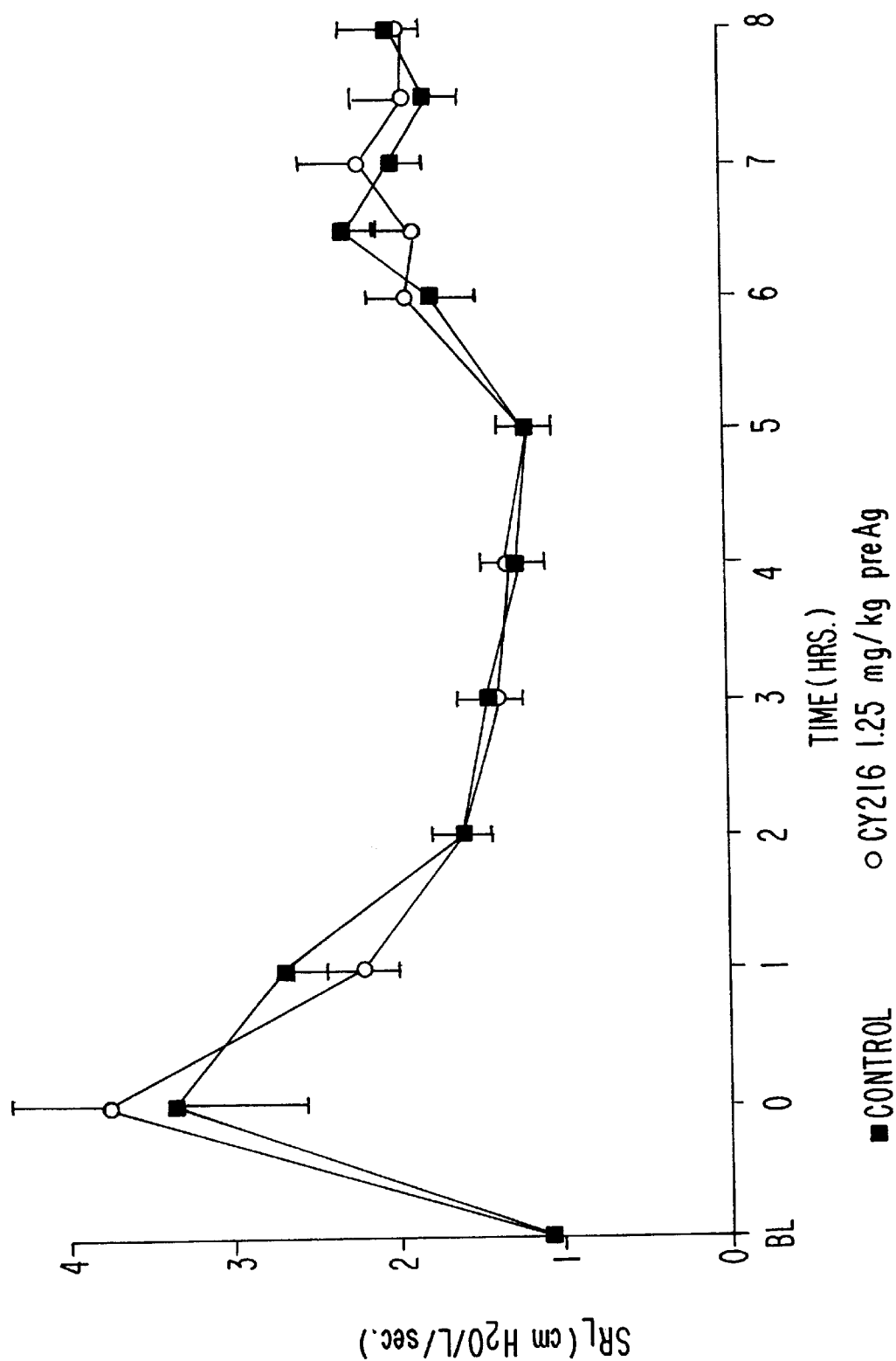

FIG. 5 is a graph illustrating the effect of pretreatment with inhaled CY-216 (avg. mol. wt. 4,270 daltons) at 1.25 mg/kg on antigen-induced bronchoconstriction in dual responder allergic sheep. Data are shown as antigen-induced mean ±SE% change in $SR_L$ in a group of animals exposed to antigen, first with no drug treatment and again several days later after pretreatment with CY-216.

Figure 6:
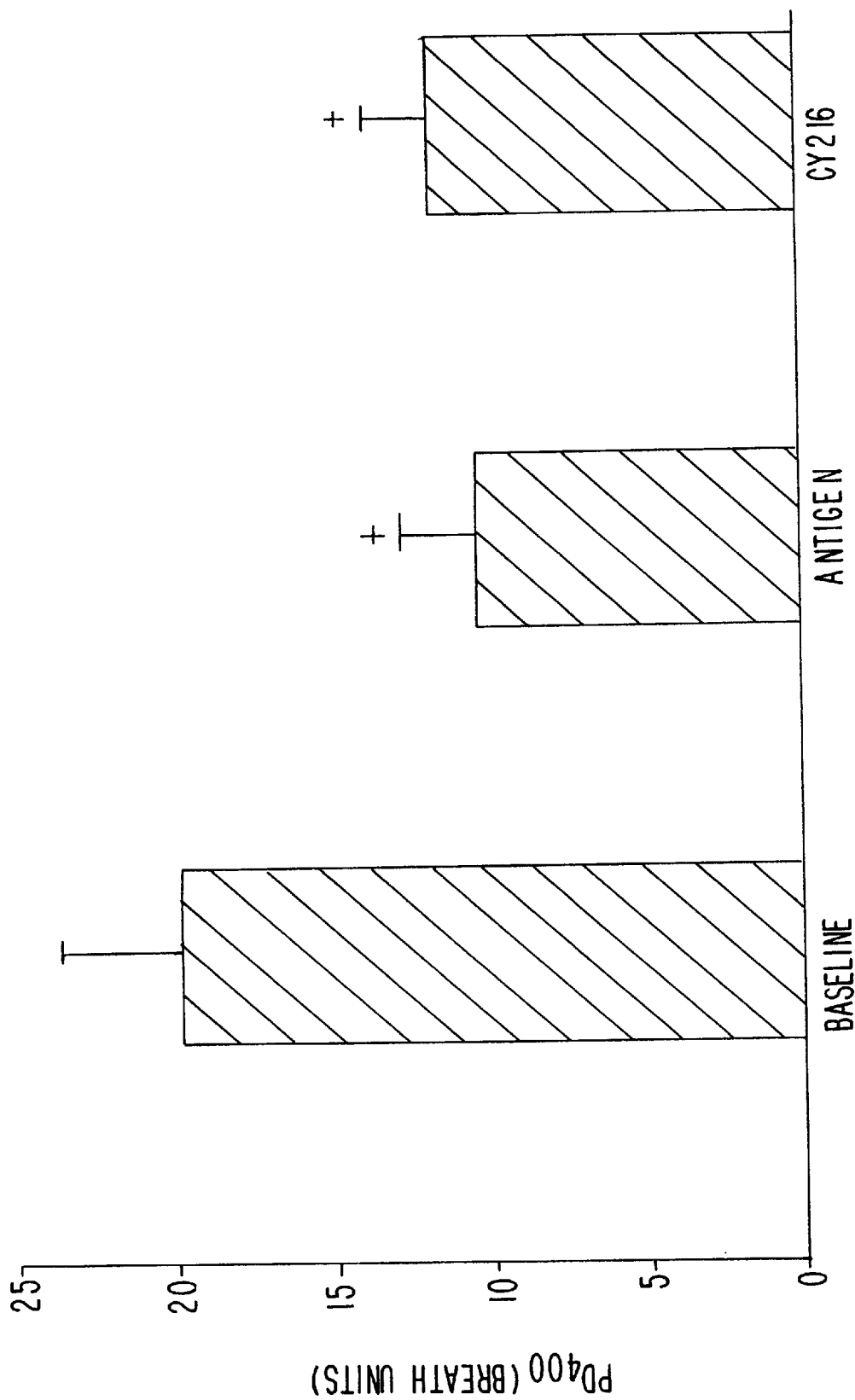

FIG. 6 is a bar graph illustrating the effect of pretreatment with inhaled CY-216 at 1.25 mg/kg on AHR in allergic sheep. Data are shown as mean ±SE $PD_{400}$ in breath units at baseline and 24 hours post-antigen challenge in a group of animals exposed to antigen, first with no drug treatment and again several days later after pretreatment with CY-216.

+=Significantly different from baseline (P<0.05)

Figure 7:
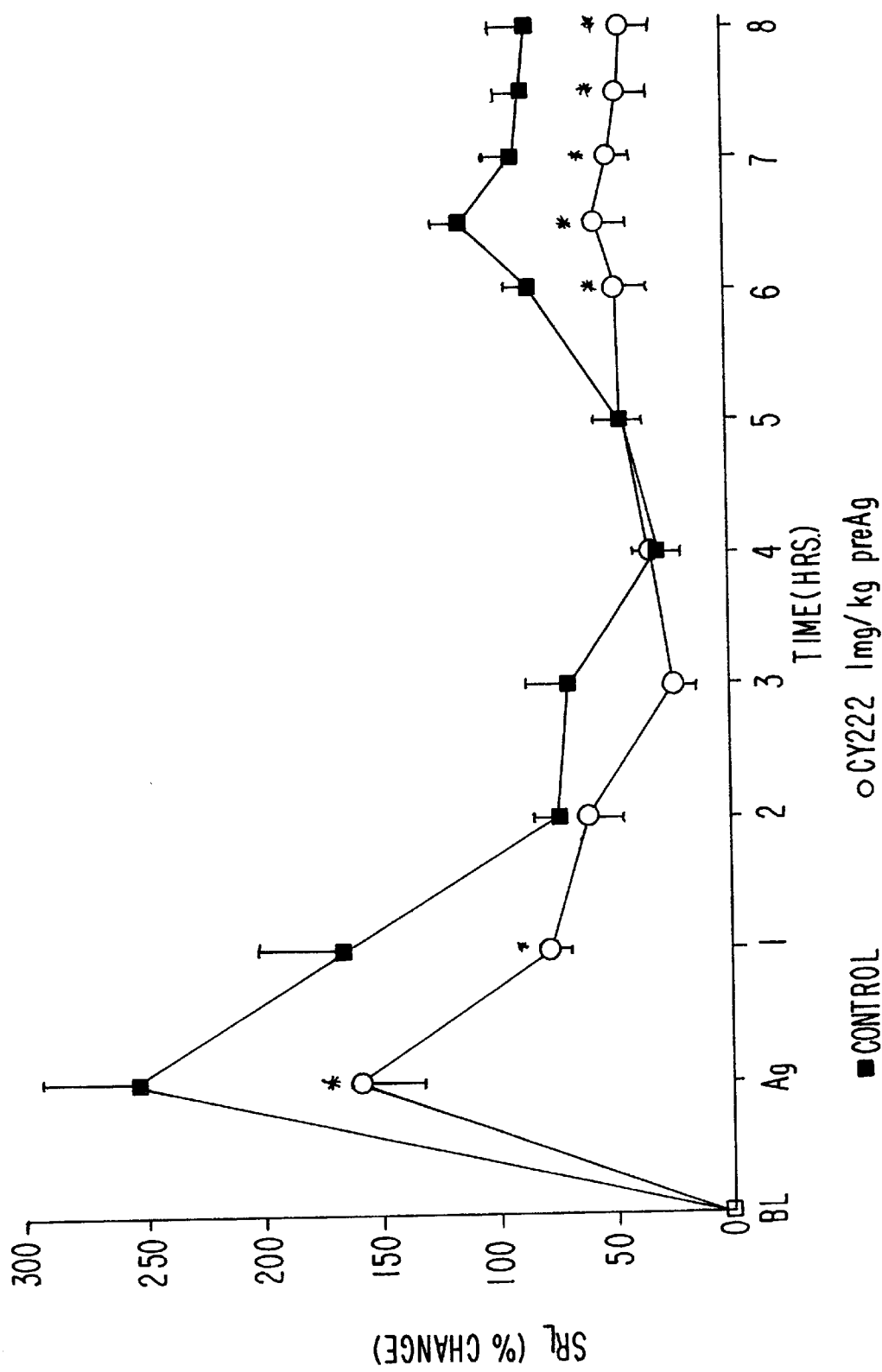

FIG. 7 is a graph illustrating the effect of pretreatment with inhaled ULMWH CY-222 (avg. mol. wt. 2,355 daltons) at 1.0 mg/kg on antigen-induced bronchoconstriction in dual responder allergic sheep. Data are shown as antigen-induced mean ±SE% change in $SR_L$ in a group of animals exposed to antigen, first with no drug treatment and again several days later after pretreatment with CY-222.

*=Significantly different from control (P<0.05)

Figure 8:
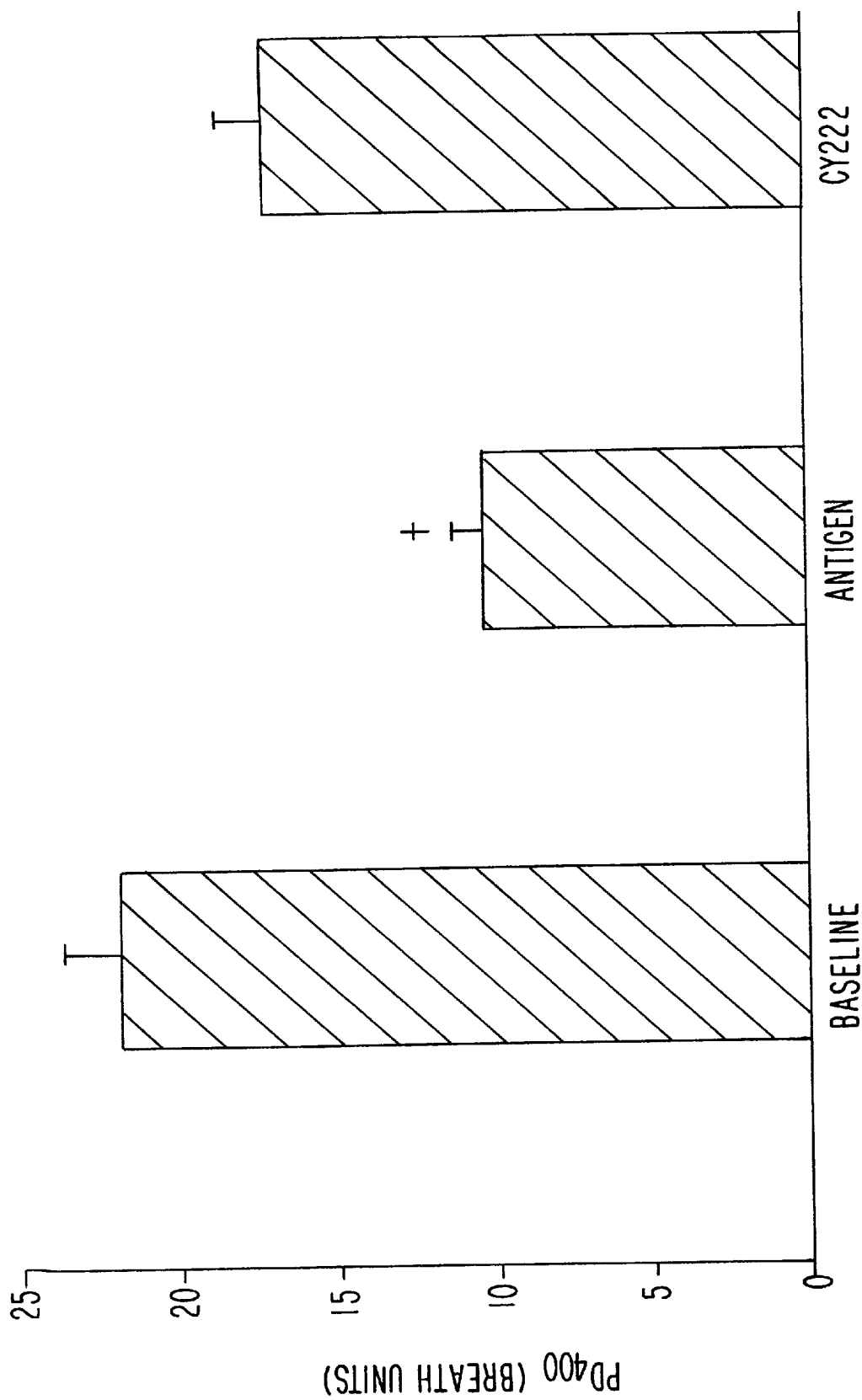

FIG. 8 is a bar graph illustrating the effect of pretreatment with inhaled CY-222 at 1.0 mg/kg on AHR in allergic sheep. Data are shown as mean ±SE $PD_{400}$ in breath units at baseline and 24 hours post-antigen challenge in a group of animals exposed to antigen, first with no drug treatment and again several days later after pretreatment with CY-222.

+=Significantly different from baseline (P<0.05)

Figure 9:
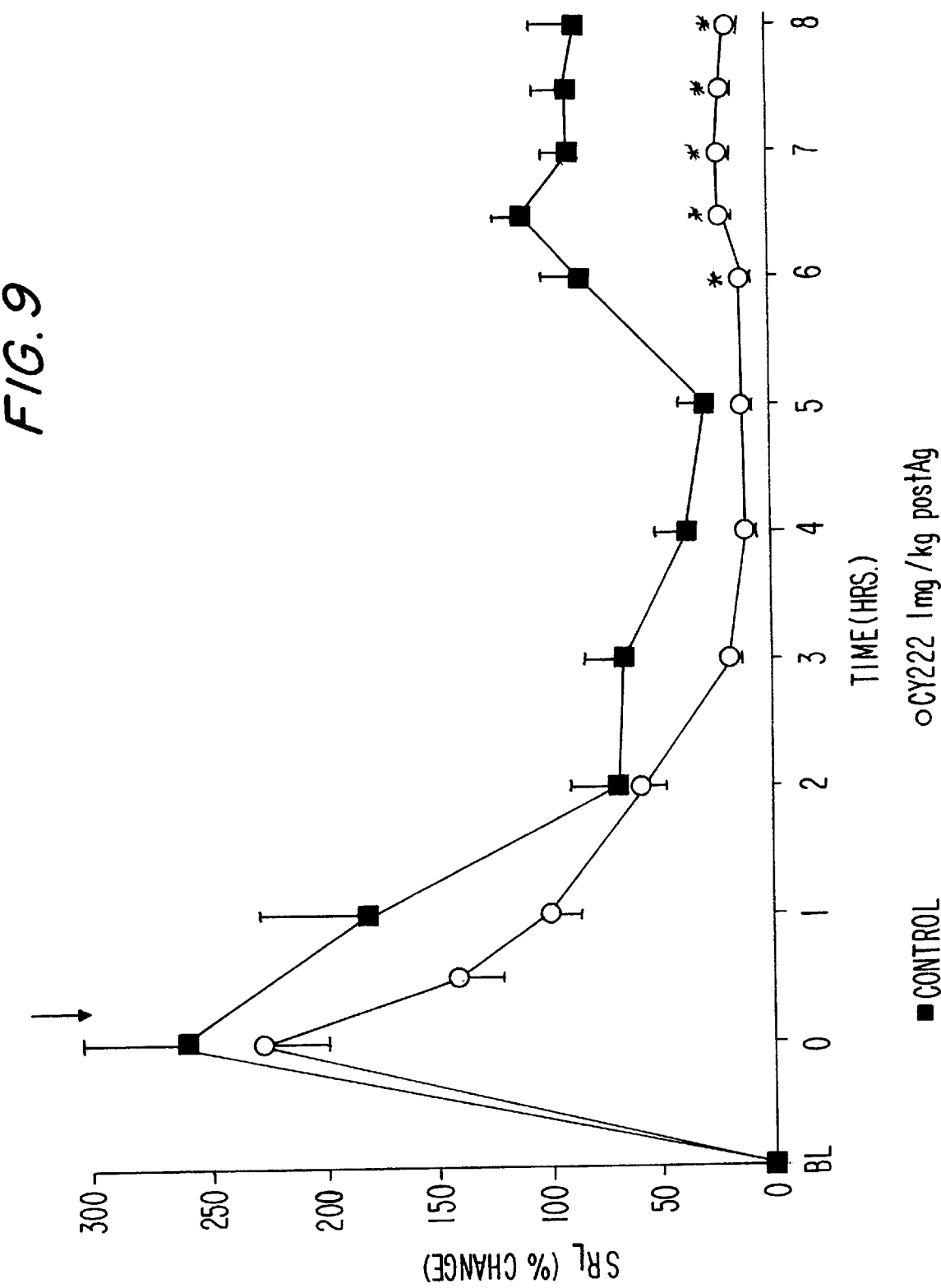

FIG. 9 is a graph illustrating the effect of treatment post-antigen challenge with inhaled CY-222 at 1.0 mg/kg on antigen-induced bronchoconstriction in dual responder allergic sheep. Data are shown as antigen-induced mean ±SE% change in $SR_L$, shown before, immediately after (time zero) and up to 8 hours post-antigen, in a group of animals exposed to antigen, first with no drug treatment and again several days later when CY-222 was administered immediately after the post-antigen measurement of $SR_L$ (arrow).

*=Significantly different from control (P<0.05)

Figure 10:
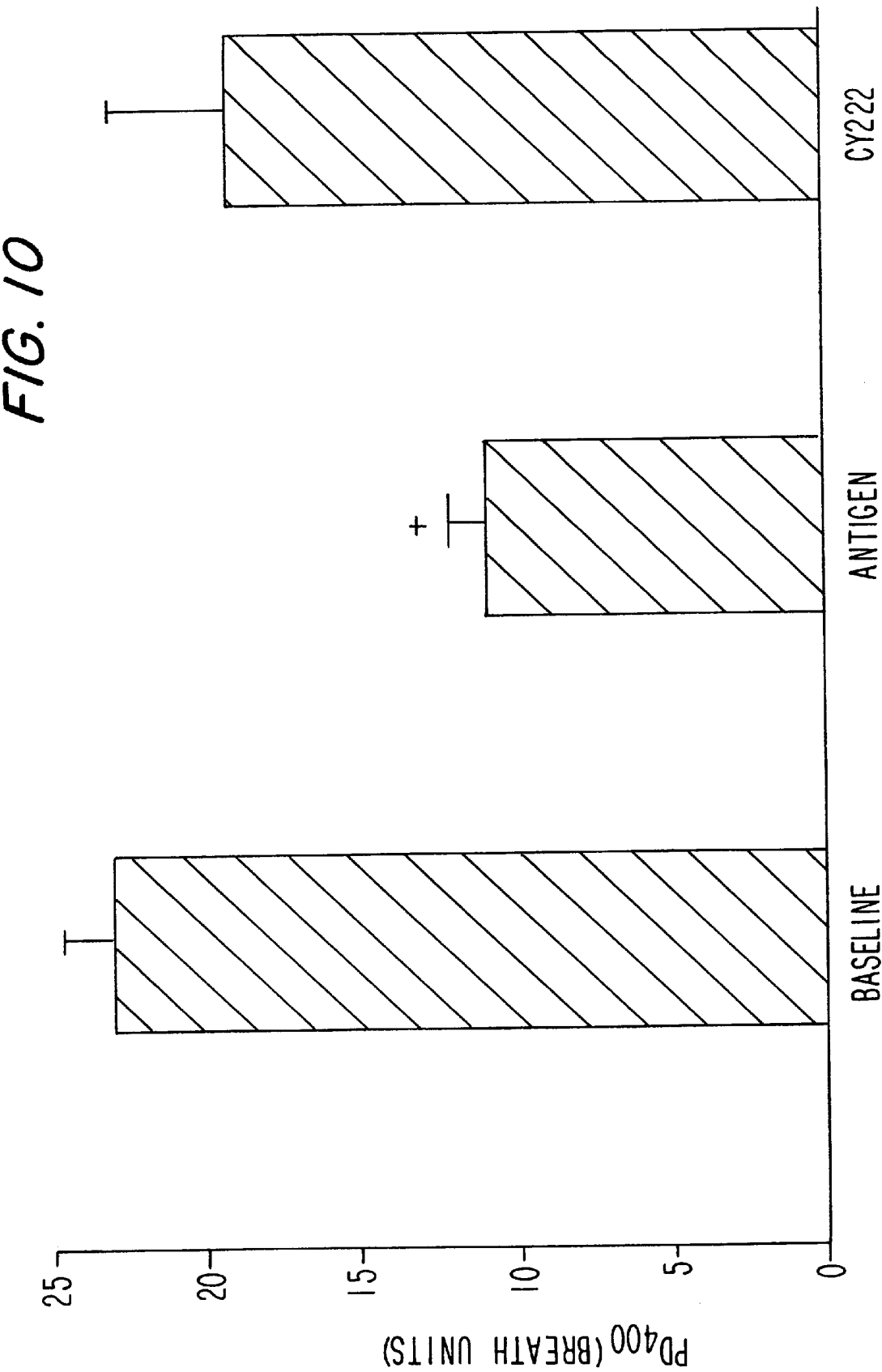

FIG. 10 is a bar graph illustrating the effect of treatment post-antigen challenge (arrow in FIG. 9) with inhaled CY-222 at 1.0 mg/kg on AHR in allergic sheep. Data are shown as mean ±SE $PD_{400}$ in breath units at baseline and 24 hours post-antigen challenge in a group of animals exposed to antigen, first with no drug treatment and again several days later when CY-222 was administered immediately after antigen challenge.

+=Significantly different from baseline (P<0.05)

Figure 11:
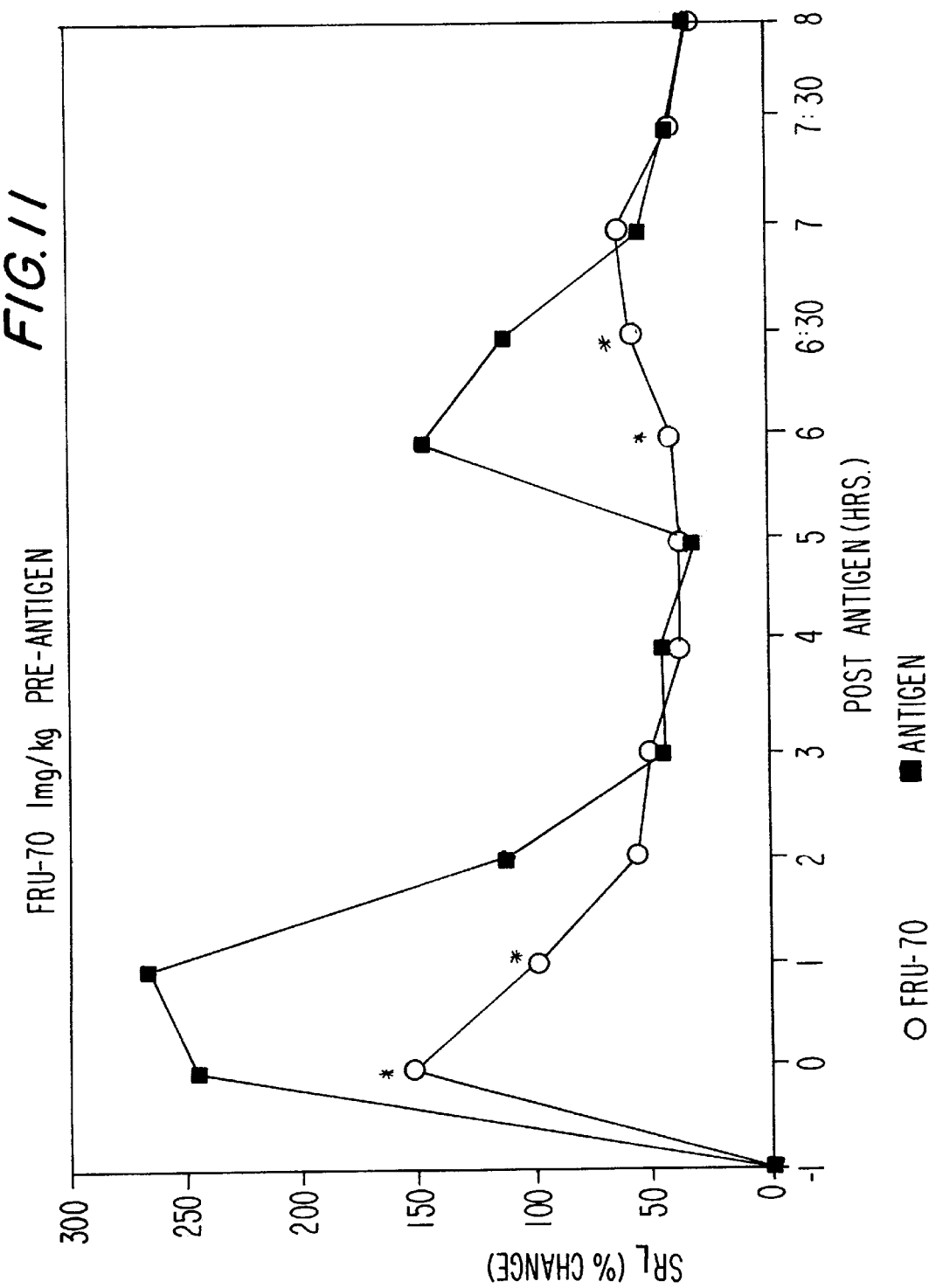

FIG. 11 is a graph illustrating the effect of pretreatment with inhaled ULMWH FRU-70 (avg. mol. wt. 2,500 daltons) at 1.0 mg/kg on antigen-induced bronchoconstriction in dual responder allergic sheep. Data are shown as antigen-induced mean ±SE% change in $SR_L$ in a group of animals exposed to antigen, first with no drug treatment and again several days later after pretreatment with FRU-70.

*=Significantly different from control (P<0.05)

Figure 12:
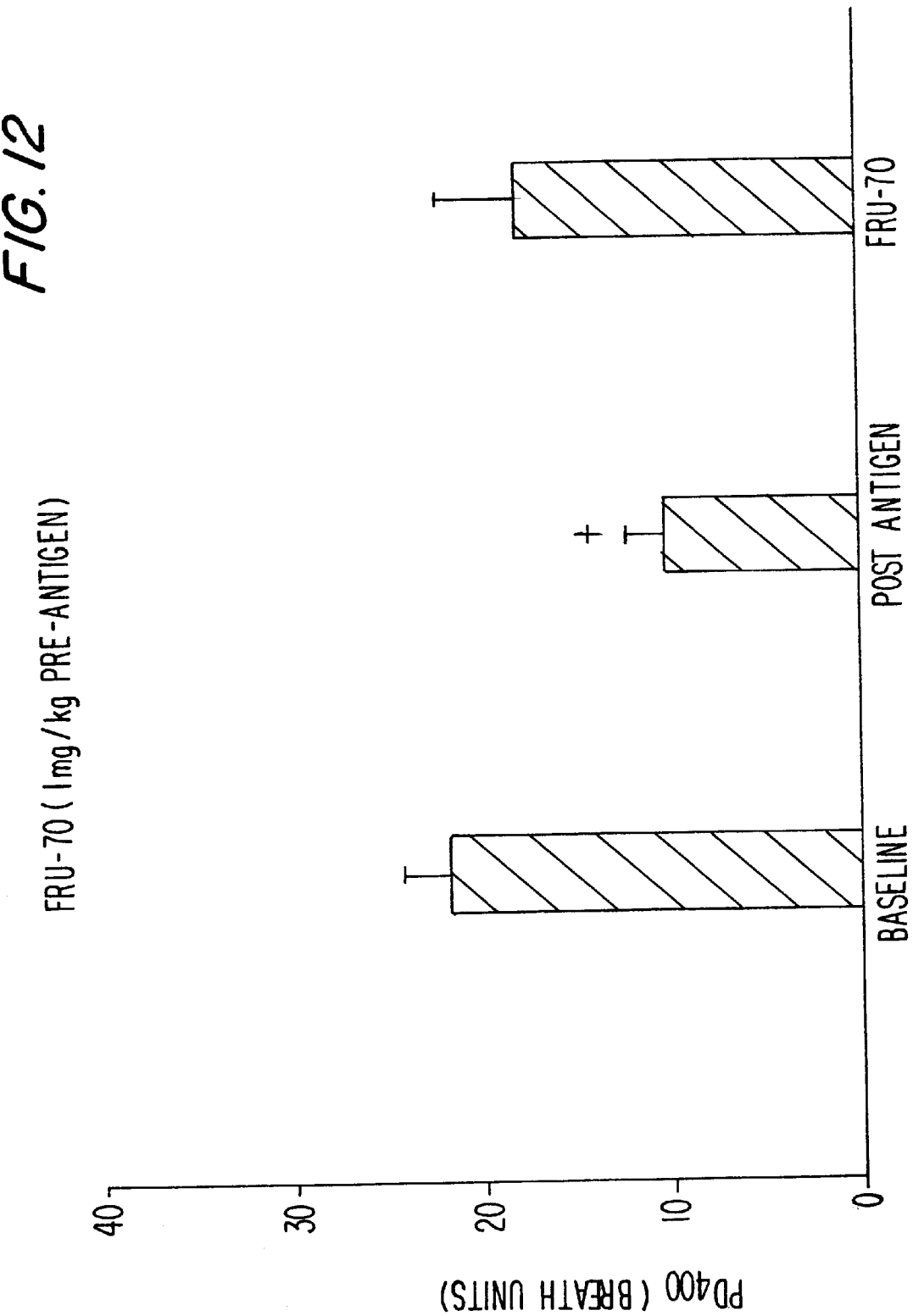

FIG. 12 is a bar graph illustrating the effect of pretreatment with inhaled FRU-70 at 1.0 mg/kg on AHR in allergic sheep. Data are shown as mean ±SE $PD_{400}$ in breath units at baseline and 24 hours post-antigen challenge in a group of animals exposed to antigen, first with no drug treatment and again several days later after pretreatment with FRU-70.

+=Significantly different from baseline (P<0.05)

Figure 13:
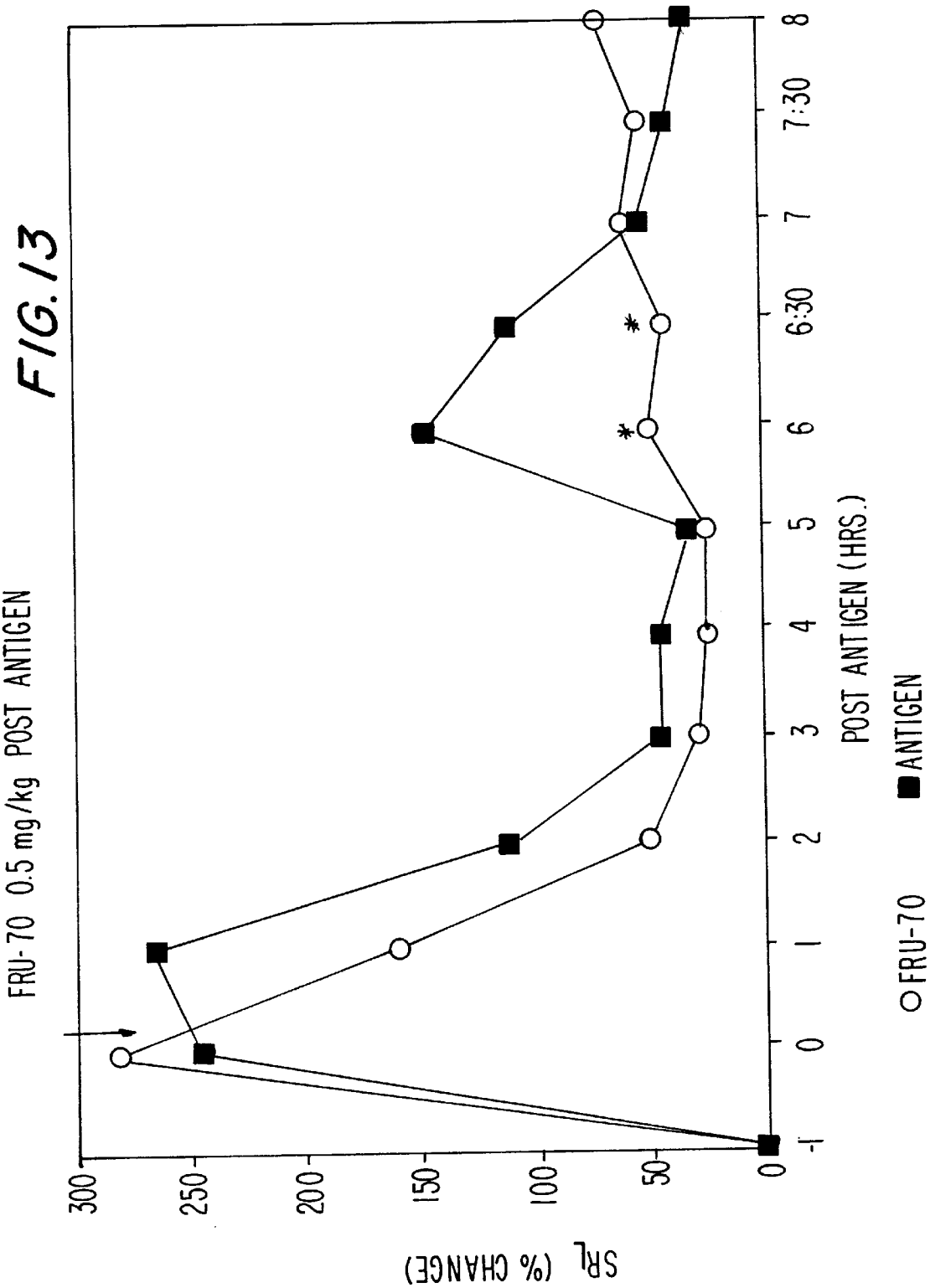

FIG. 13 is a graph illustrating the effect of treatment post-antigen challenge with inhaled FRU-70 at 0.5 mg/kg on antigen-induced bronchoconstriction in dual responder allergic sheep. Data are shown as antigen-induced mean ±SE% change in $SR_L$, shown before, immediately after (time zero) and up to 8 hours post-antigen, in a group of animals exposed to antigen, first with no drug treatment and again several days later when FRU-70 was administered immediately after the post-antigen measurement of $SR_L$ (arrow).

*=Significantly different from control (P<0.05)

Figure 14:
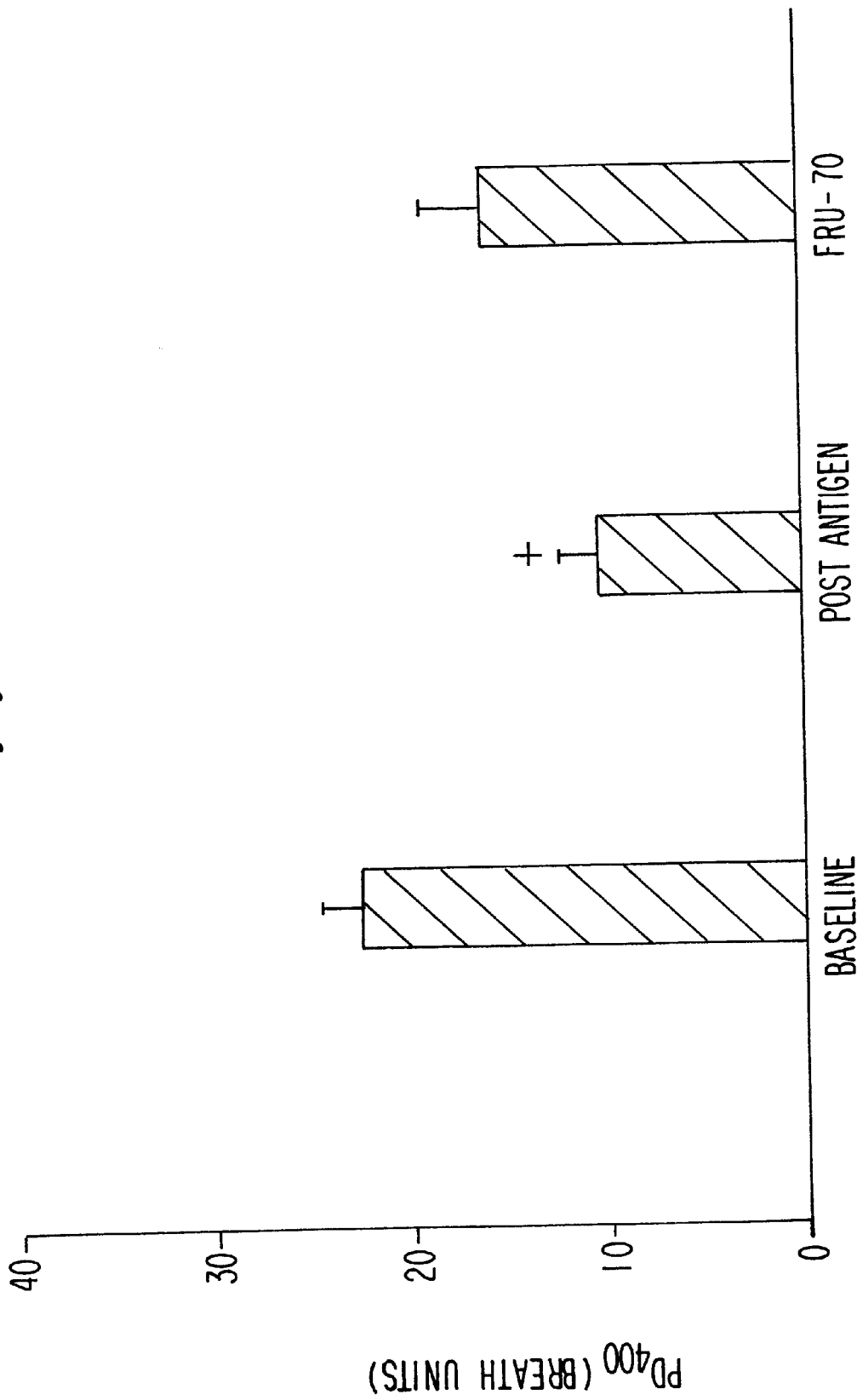

FIG. 14 is a bar graph illustrating the effect of treatment post-antigen challenge (arrow in FIG. 13) with inhaled FRU-70 at 0.5 mg/kg on AHR in allergic sheep. Data are shown as mean ±SE $PD_{400}$ in breath units at baseline and 24 hours post-antigen challenge in a group of animals exposed to antigen, first with no drug treatment and again several days later when FRU-70 was administered immediately after antigen challenge.

+=Significantly different from baseline (P<0.05)

Figure 15:
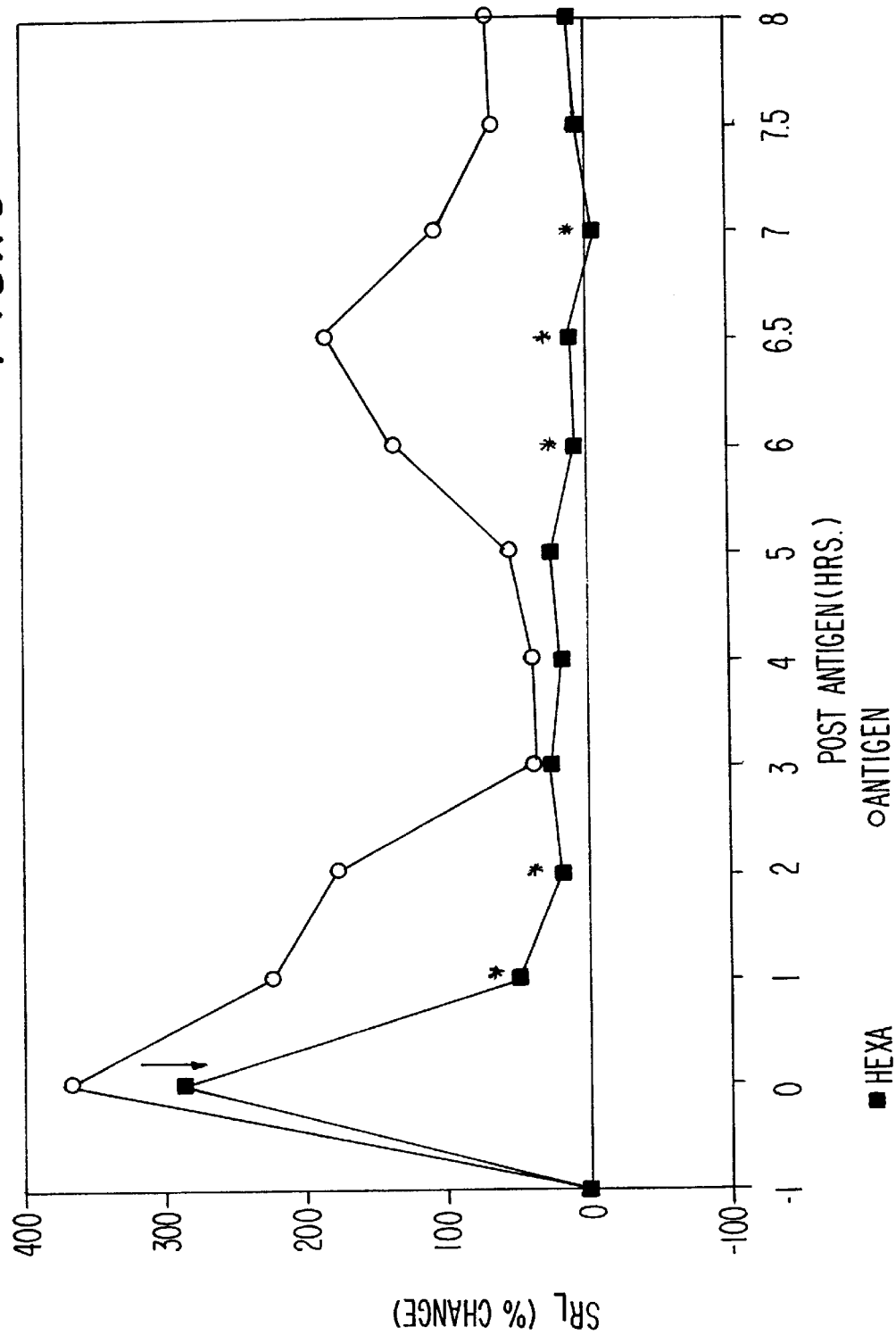

FIG. 15 is a graph illustrating the effect of treatment post-antigen challenge with inhaled hexasaccharide mixture (avg. mol. wt. 1,930 daltons) at 0.5 mg/kg on antigen-induced bronchoconstriction in dual responder allergic sheep. Data are shown as antigen-induced mean ±SE% change in $SR_L$, shown before, immediately after (time zero) and up to 8 hours post-antigen, in a group of animals exposed to antigen, first with no drug treatment and again several days later when the hexasaccharide mixture was administered immediately after the post-antigen measurement of $SR_L$ (arrow).

*=Significantly different from control (P<0.05)

Figure 16:
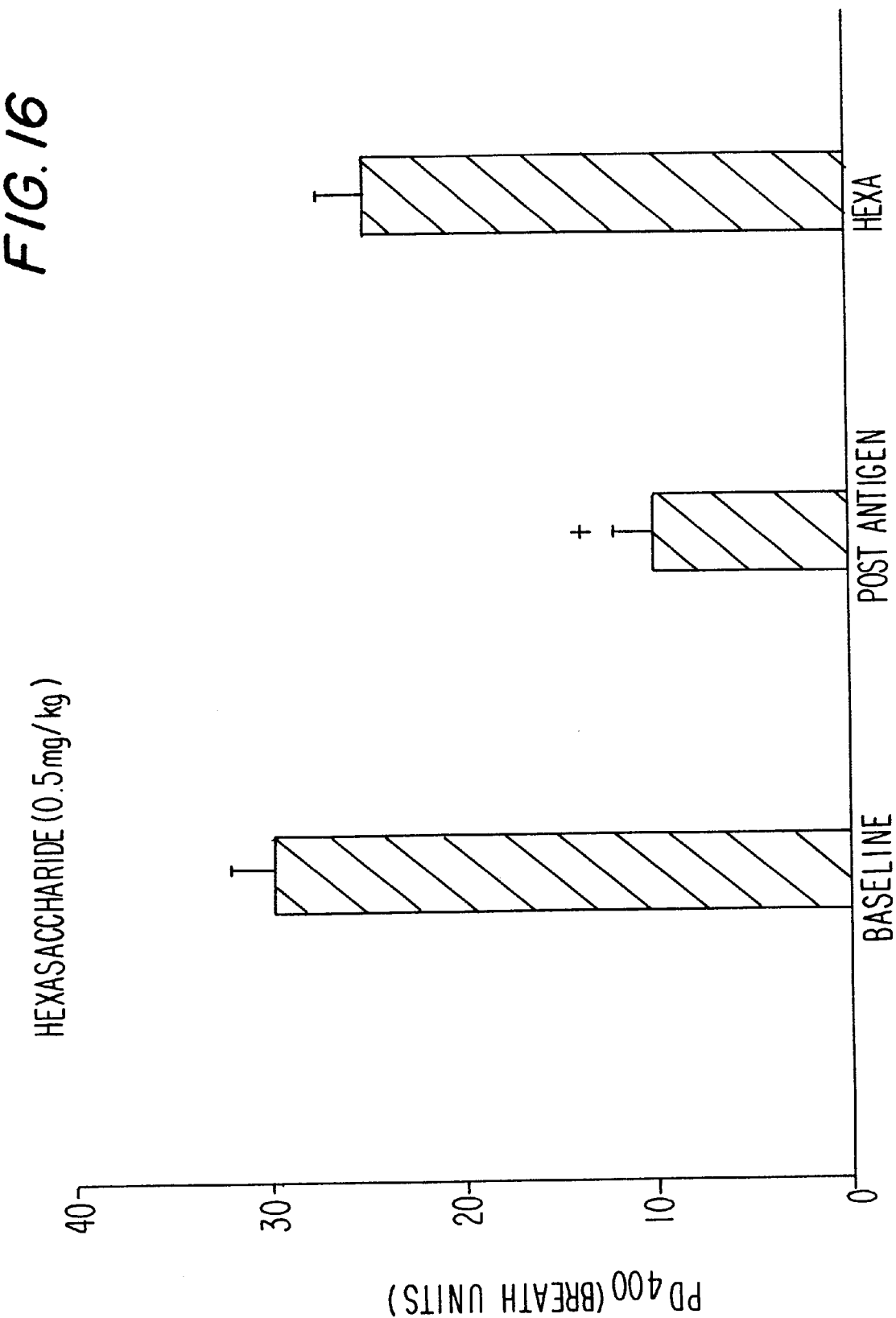

FIG. 16 is a bar graph illustrating the effect of treatment post-antigen challenge (arrow in FIG. 15) with inhaled hexasaccharide mixture at 0.5 mg/kg on AHR in allergic sheep. Data are shown as mean ±SE $PD_{400}$ in breath units at baseline and 24 hours post-antigen challenge in a group of animals exposed to antigen, first with no drug treatment and again several days later when the hexasaccharide mixture was administered immediately after antigen challenge.

+=Significantly different from baseline (P<0.05)

Figure 17:
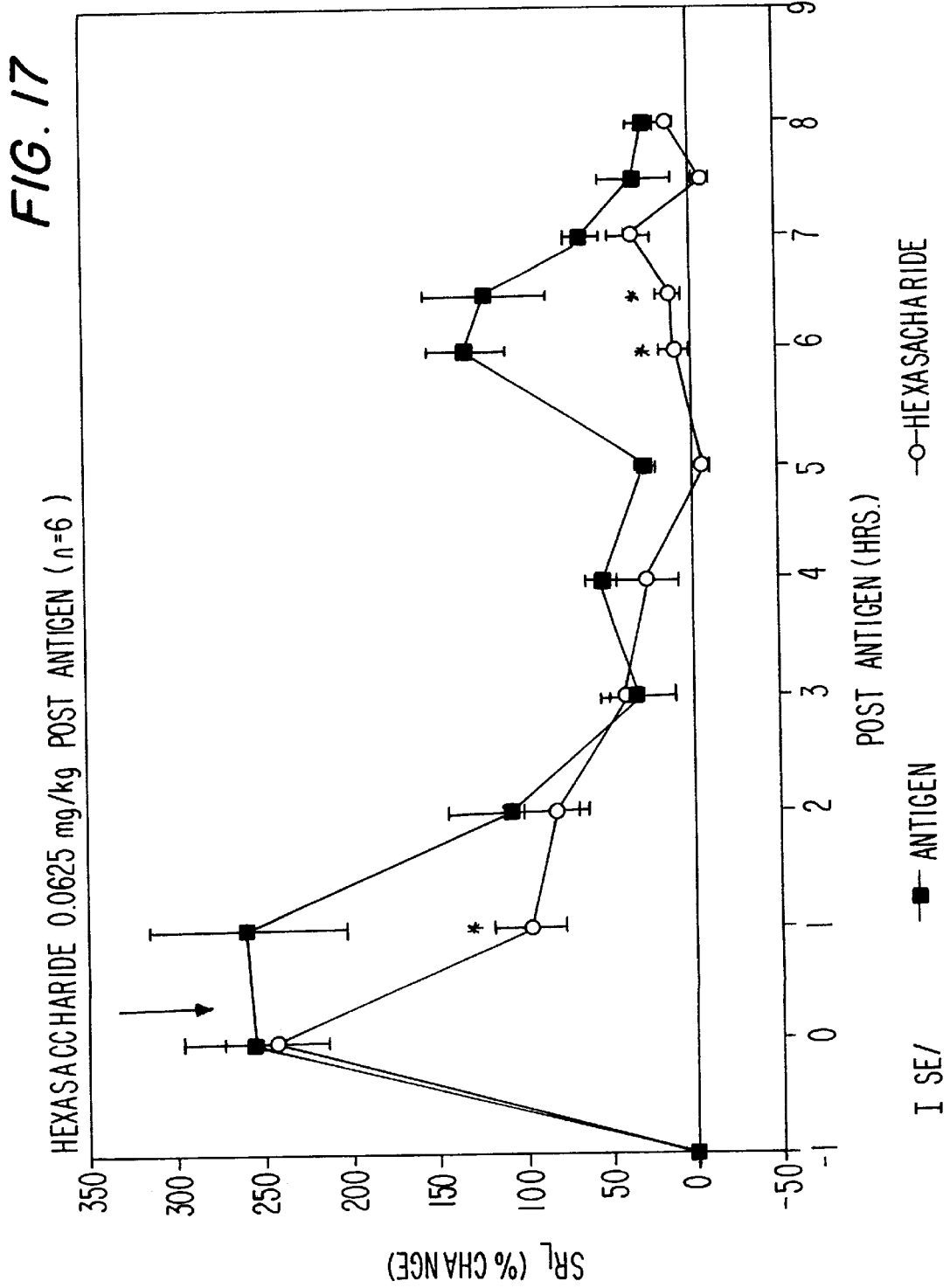

FIG. 17 is a graph illustrating the effect of treatment post-antigen challenge with inhaled purified hexasaccharide (avg. mol. wt. 1998 daltons) at 0.062 mg/kg on antigen-induced bronchoconstriction in dual responder allergic sheep. Data are shown as antigen-induced mean ±SE% change in $SR_L$, shown before, immediately after (time zero) and up to 8 hours post-antigen, in a group of animals exposed to antigen, first with no drug treatment and again several days later when the hexasaccharide was administered immediately after the post-antigen measurement of $SR_L$ (arrow).

*=Significantly different from control (P<0.05)

Figure 18:
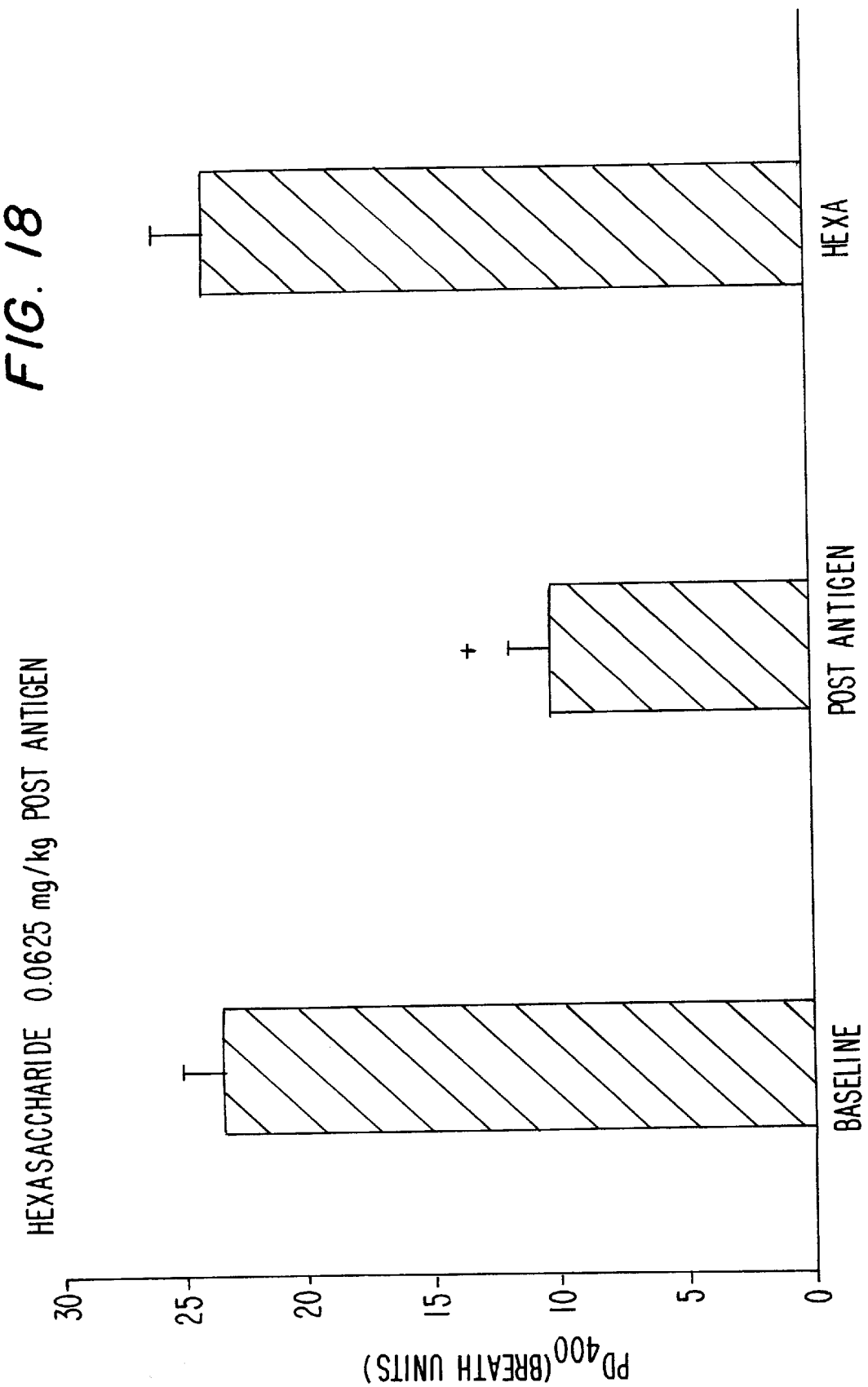

FIG. 18 is a bar graph illustrating the effect of treatment post-antigen challenge (arrow in FIG. 17) with inhaled purified hexasaccharide at 0.062 mg/kg on AHR in allergic sheep. Data are shown as mean ±SE $PD_{400}$ in breath units at baseline and 24 hours post-antigen challenge first, with no drug treatment and again several days later when the hexasaccharide was administered immediately after antigen challenge.

+=Significantly different from baseline (P<0.05)

Figure 19:
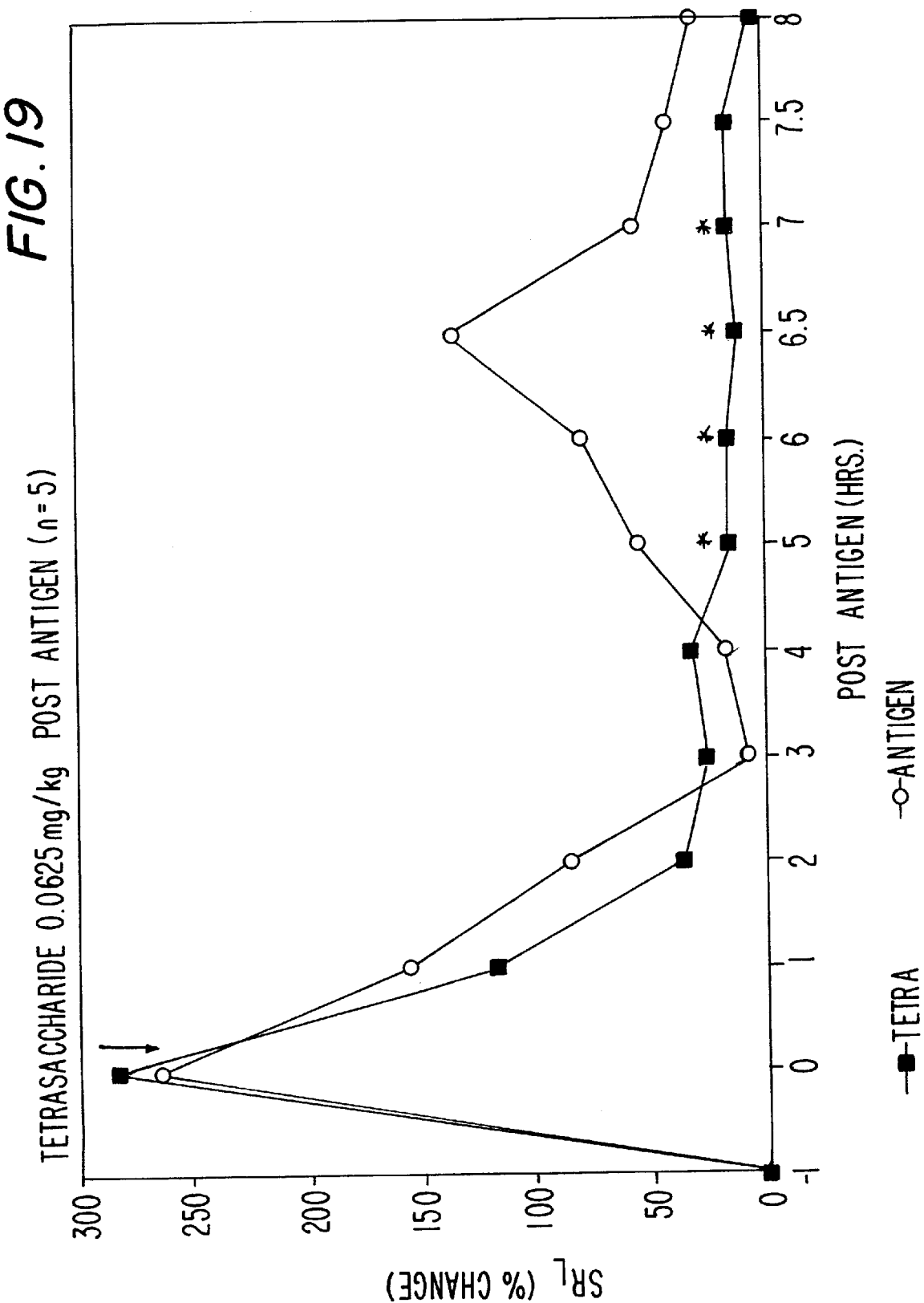

FIG. 19 is a graph illustrating the effect of treatment post-antigen challenge with inhaled purified tetrasaccharide (avg. mol. wt. 1290 daltons) at 0.062 mg/kg on antigen-induced bronchoconstriction in dual responder allergic sheep. Data are shown as antigen-induced mean ±SE% change in $SR_L$, shown before, immediately after (time zero) and up to 8 hours post-antigen, in a group of animals exposed to antigen, first with no drug treatment and again several days later when the tetrasaccharide was administered immediately after the post-antigen measurement of $SR_L$ (arrow).

*=Significantly different from control (P<0.05)

Figure 20:
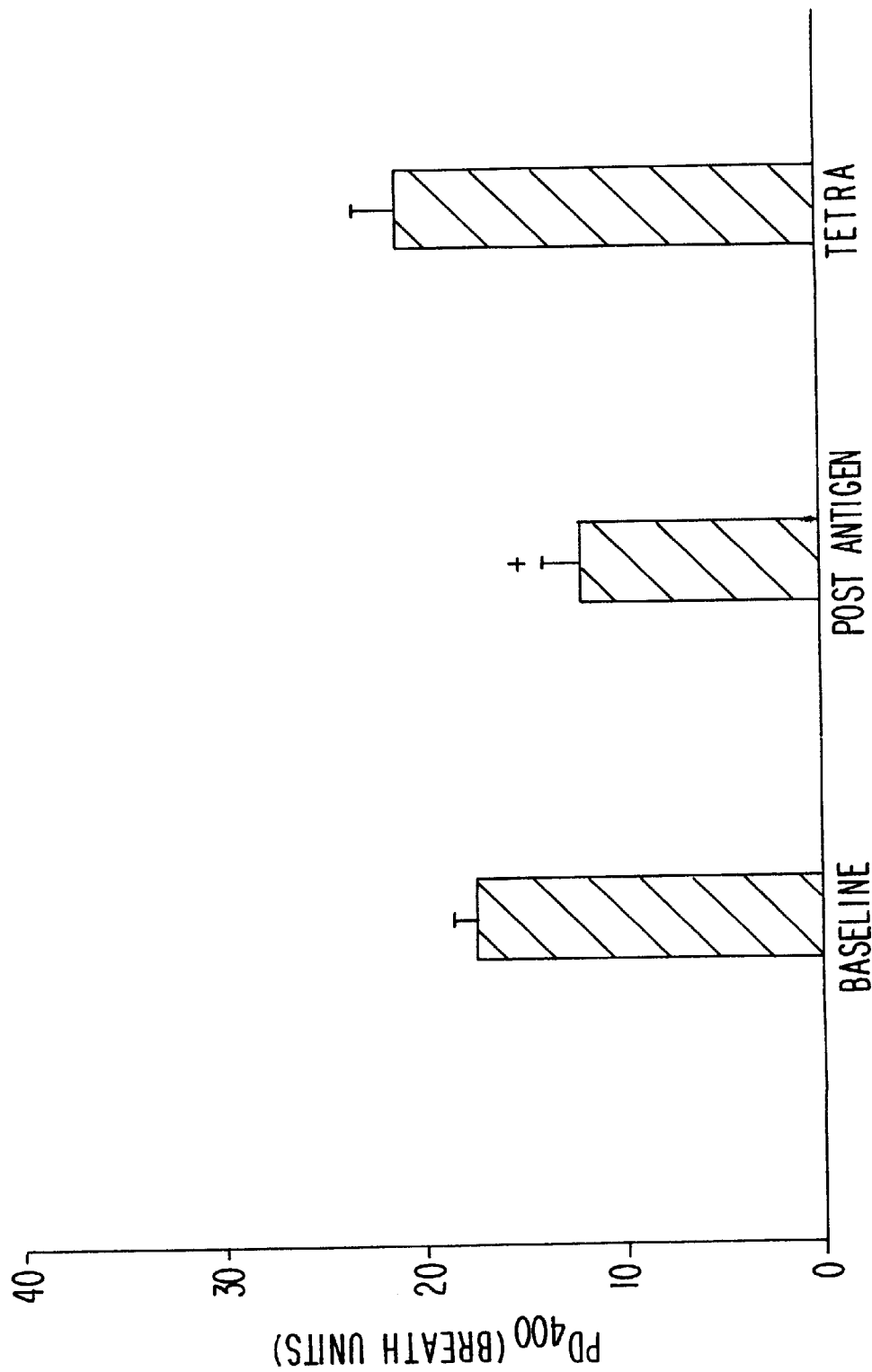

FIG. 20 is a bar graph illustrating the effect of treatment post-antigen challenge (arrow in FIG. 19) with inhaled purified tetrasaccharide at 0.062 mg/kg on AHR in allergic sheep. Data are shown as mean ±SE $PD_{400}$ in breath units at baseline and 24 hours post-antigen challenge first, with no drug treatment and again several days later when the tetrasaccharide was administered immediately after antigen challenge.

+=Significantly different from baseline (P<0.05)

Figure 21:
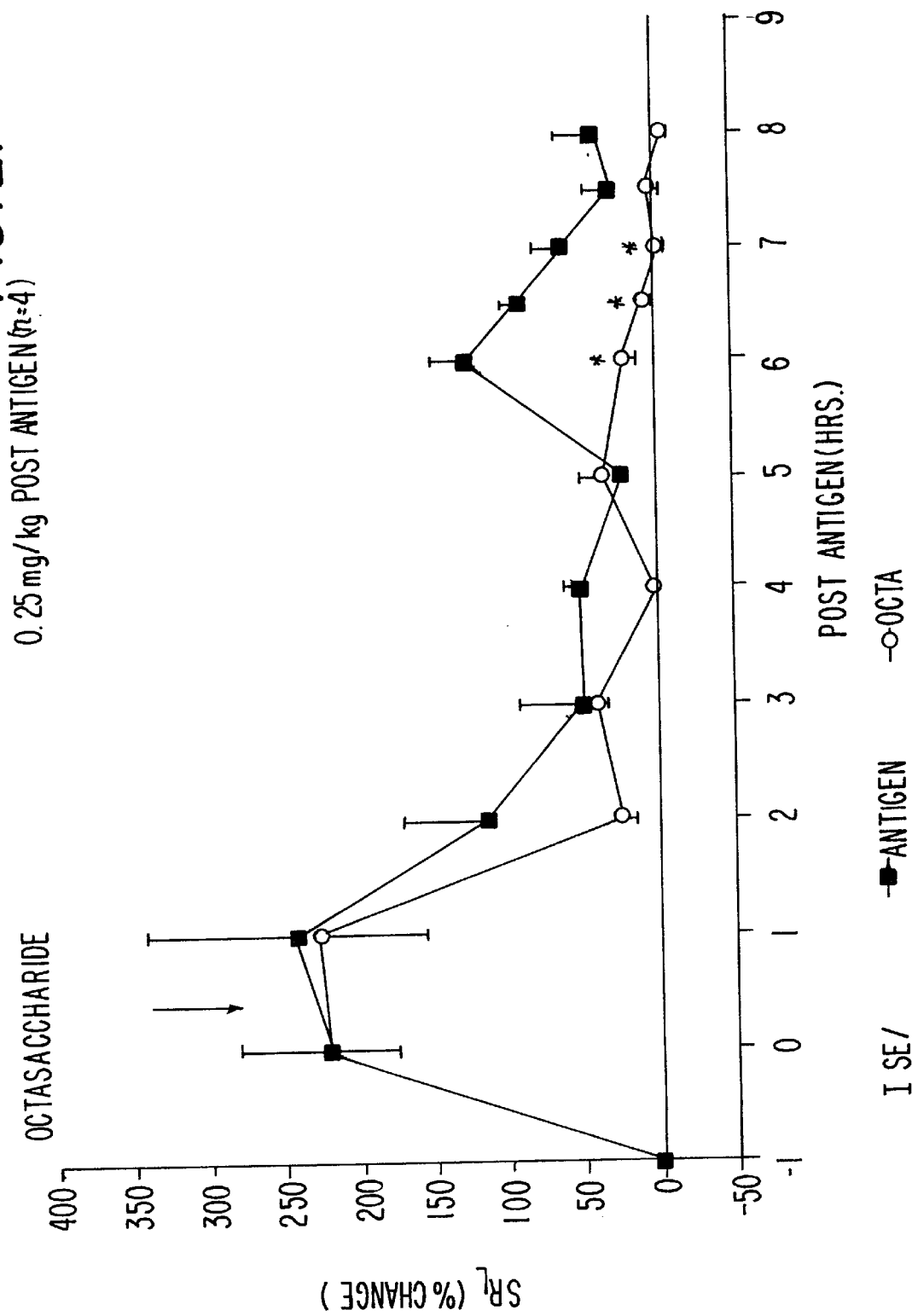

FIG. 21 is a graph illustrating the effect of treatment post-antigen challenge with inhaled octasaccharide (avg. mol. wt. 2,480 daltons) at 0.25 mg/kg on antigen-induced bronchoconstriction in dual responder allergic sheep. Data are shown as antigen-induced mean ±SE% change in $SR_L$, shown before, immediately after (time zero) and up to 8 hours post-antigen, in a group of animals exposed to antigen, first with no drug treatment and again several days later when the octasaccharide mixture was administered immediately after the post-antigen measurement of $SR_L$ (arrow).

*=Significantly different from control (P<0.05)

Figure 22:
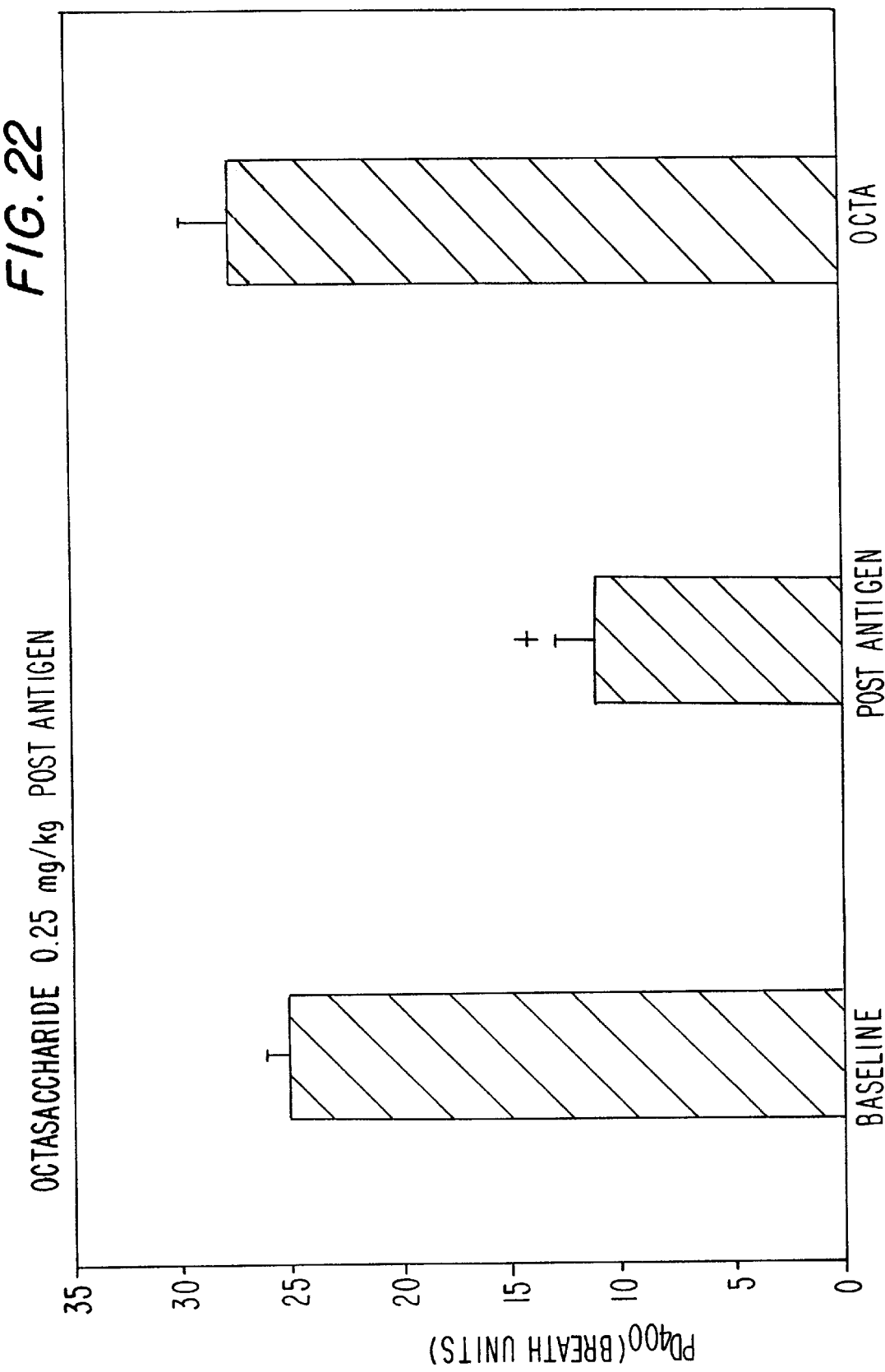

FIG. 22 is a bar graph illustrating the effect of treatment post-antigen challenge (arrow in FIG. 21) with inhaled octasaccharide at 0.25 mg/kg on AHR in allergic sheep. Data are shown as mean ±SE $PD_{400}$ in breath units at baseline and 24 hours post-antigen challenge in a group of animals exposed to antigen, first with no drug treatment and again several days later when the octasaccharide was administered immediately after antigen challenge.

+=Significantly different from baseline (P<0.05)

Figure 23:
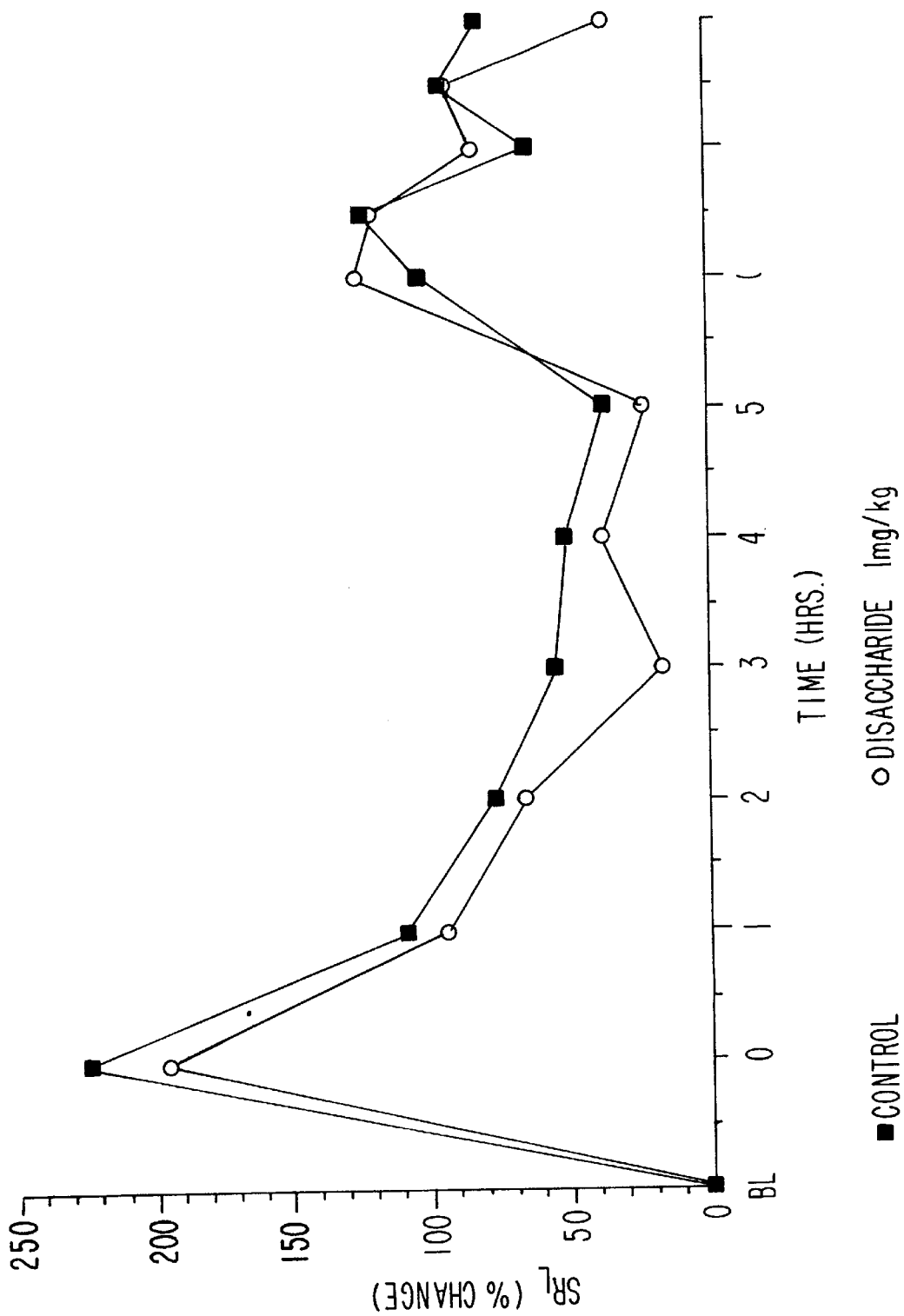

FIG. 23 is a graph illustrating the effect of pretreatment with inhaled disaccharide (avg. mol. wt. 660 daltons) at 1.0 mg/kg on antigen-induced bronchoconstriction in dual responder allergic sheep. Data are shown as antigen-induced mean ±SE% change in $SR_L$, shown before, immediately after (time zero) and up to 8 hours post-antigen, in a group of animals exposed to antigen, first with no drug treatment and again several days later after pretreatment with disaccharide.

Figure 24:
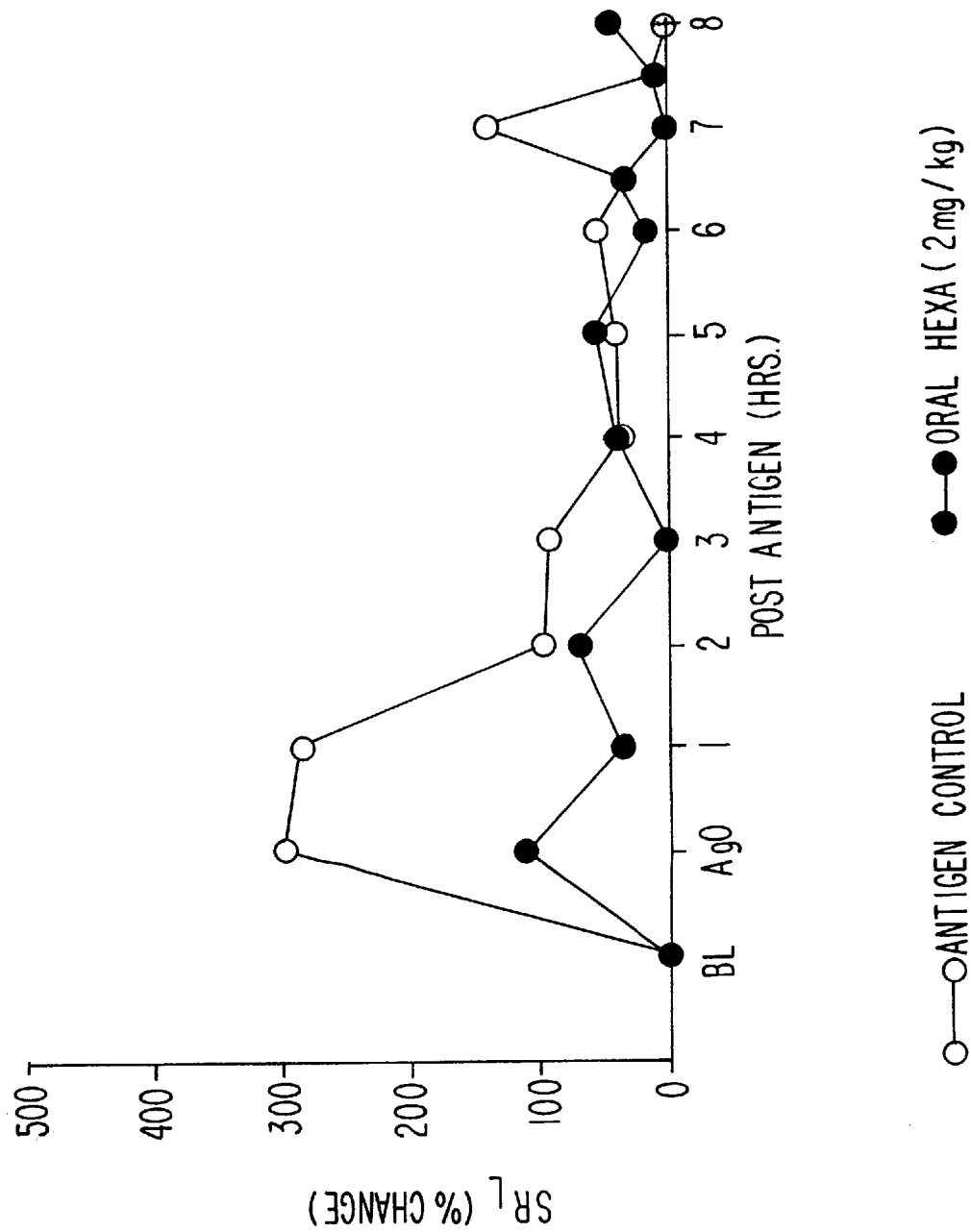

FIG. 24 is a graph illustrating the effect of pretreatment with orally administered purified hexasaccharide (avg. mol. wt. 1,998 daltons) at 2.0 mg/kg on antigen-induced bronchoconstriction in a dual responder allergic sheep. Data are shown as antigen-induced an ±SE % change in $SR_L$ in a single sheep exposed to antigen, first with no drug treatment and again several days later after pretreatment with hexasaccharide.

Figure 25:
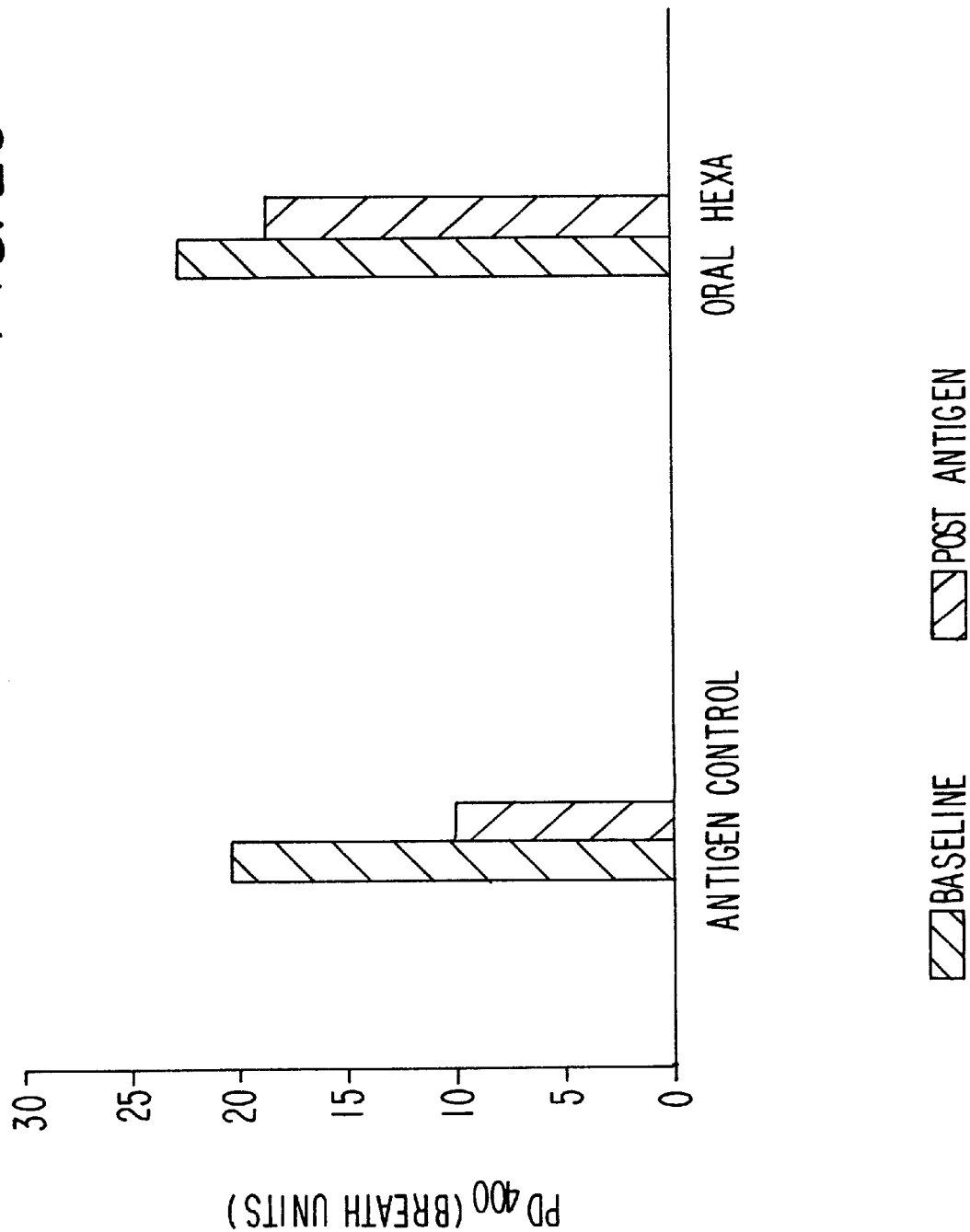

FIG. 25 is a bar graph illustrating the effect of pretreatment with orally administered purified hexasaccharide at 2.0 mg/kg on AHR in an allergic sheep. Data are shown as mean ±SE $PD_{400}$ in breath units at baseline and 24 hours post-antigen challenge in a single sheep exposed to antigen, first with no drug treatment and again several days later after pretreatment with hexasaccharide.

Figure 26:
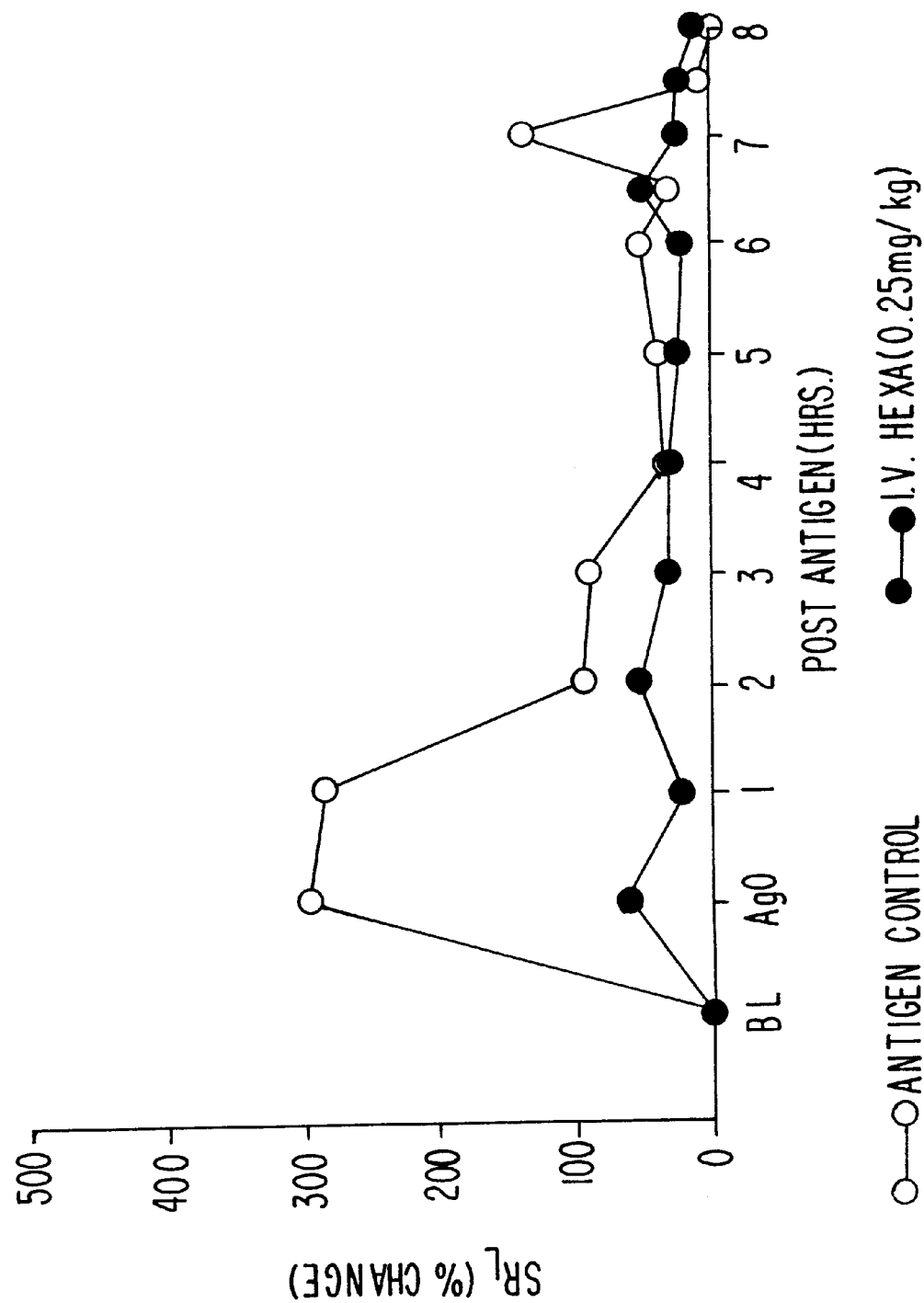

FIG. 26 is a graph illustrating the effect of pretreatment with intravenously administered purified hexasaccharide (avg. mol. wt. 1,998 daltons) at 0.25 mg/kg on antigen-induced bronchoconstriction in a dual responder allergic sheep. Data are shown as antigen-induced mean ±SE% change in $SR_L$ in a single sheep exposed to antigen, first with no drug treatment and again several days later after pretreatment with hexasaccharide.

Figure 27:
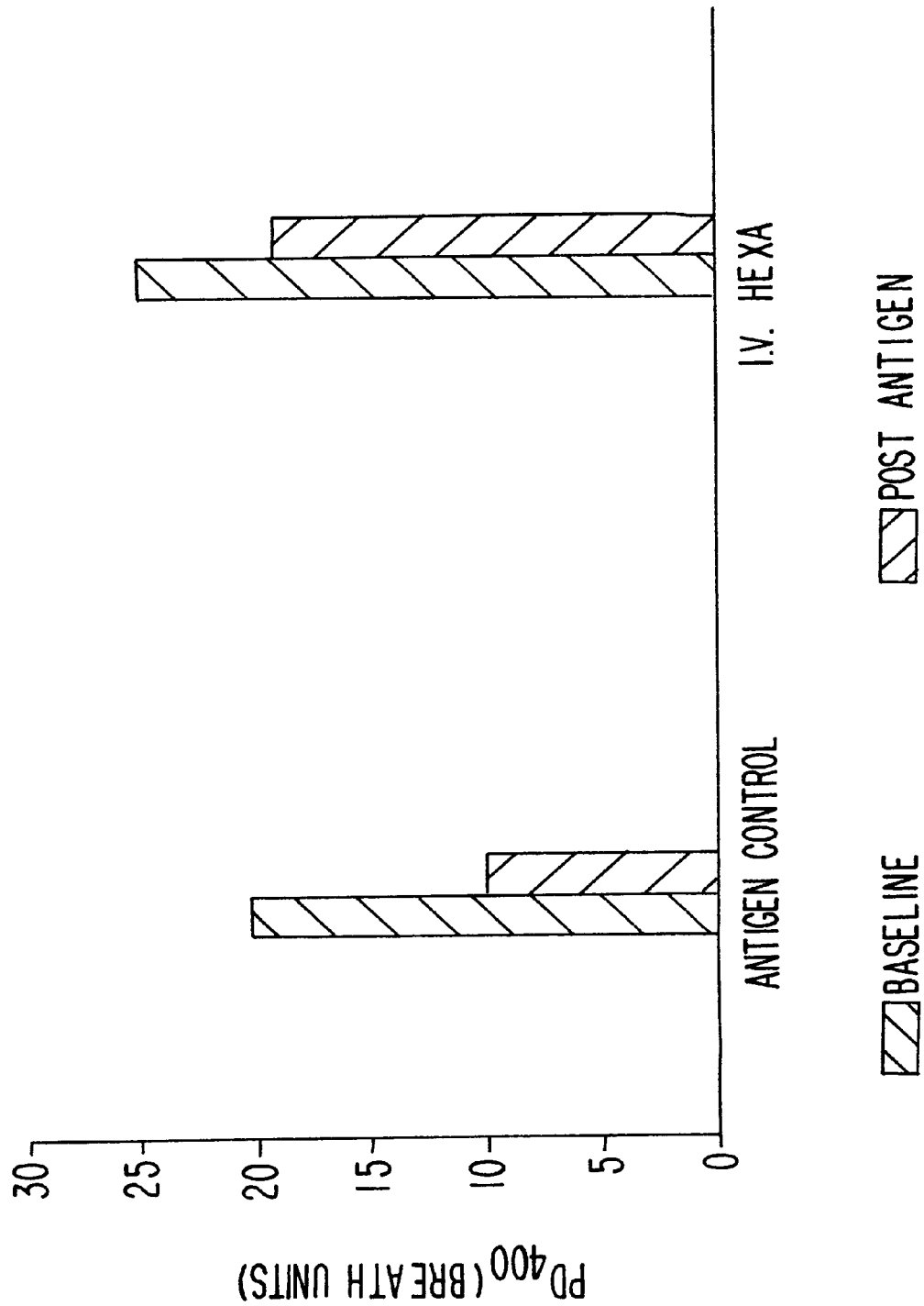

FIG. 27 is a bar graph illustrating the effect of pretreatment with intravenously administered purified hexasaccharides at 0.25 mg/kg on AHR in allergic sheep. Data are shown as mean ±SE $PD_{400}$ in breath units at baseline and 24 hours post-antigen challenge in a single sheep exposed to antigen, first with no drug treatment and again several days later after pretreatment with hexasaccharide.

FIG. 28 is a bar graph illustrating the comparative activity in preventing antigen-induced eosinophil influx in the bronchoalveolar lavage fluid of three groups of mice administered, respectively, inhaled, oral and intraperitoneal purified hexasaccharide.

DETAILED DESCRIPTION OF THE INVENTION

The present invention pertains generally to a method of treatment of mammalian patients suffering from or prone to development of disease conditions characterized by late phase allergic reactions and/or by inflammatory reactions, as well as novel pharmaceutical compositions containing ultra-low molecular weight heparins which are suitable for use in practicing said method.

Heparin, a sulfated mucopolysaccharide, is synthesized in mast cells as a proteoglycan and is particularly abundant in the lungs of various animals. Heparin is not a specific compound of fixed molecular weight but is actually a heterogenous mixture of variably sulfated polysaccharide chains composed of repeating units of D-glucosamine and either L-iduronic or D-glucuronic acids. The average molecular weight of heparin isolated from animal tissues ranges from about 6,000 to about 30,000 daltons.

Pharmacologically, heparin is known primarily as an anticoagulant. This activity results from heparin's ability to bind to some of the residues of antithrombin III (AT-III), accelerating the neutralization by AT-III of activated clotting factors and preventing the conversion of prothrombin to thrombin. Larger amounts of heparin can inactivate thrombin and earlier clotting factors, preventing conversion of fibrinogen to fibrin.

The hemorrhagic activity of heparin is related to the molecular weight of its polysaccharide fragments; low molecular weight components or fragments (for example, fragments having a molecular weight of less than 6,000 daltons) have moderate to low antithrombin and hemorrhagic effects. Similarly, low molecular weight heparins isolated from animal tissue generally have reduced hemorraghic properties compared to commercial heparin but may still have significant anticoagulant activity.

Commercial heparin, which is generally derived from beef lung or pork intestinal mucosa, has an average molecular weight of about 15,000–17,500 daltons.

Heparin has been shown to act as a specific blocker of the $IP_3$ receptors and inhibits $IP_3$ mediated calcium release. We have previously suggested that heparin may block $IP_3$ receptors in mast cells and therefore by interfering with signal transduction may modulate mast cell degranulation and mediator release. In vivo and in vitro studies support this concept and have demonstrated that inhaled heparin can attenuate allergic bronchoconstriction in sheep, prevent exercise induced asthma, as well as inhibit anti IgE induced mast cell histamine release. Inhaled heparin in doses up to 1,000 units/kg has been found to have no effect on partial thromboplastin time (PTT), thus, suggesting a "non-anticoagulant" effect.

It has also been reported that low molecular weight heparins (average molecular weight about 4,500 daltons), which have reduced APTT activity, were effective in animal studies in preventing antigen-induced bronchoconstrictor response (ABR) and bronchial hyperreactivity, also referred to as airway-hyperresponsiveness (AHR). However, as discussed and illustrated in greater detail below, neither commercial heparin nor medium or low molecular weight heparins, even those with very low anticoagulant activity, are effective in ameliorating AHR subsequent to antigen challenge in test animals. These heparins apparently provide only a prophylactic, preventive effect, but are not of value in treating an antigen-triggered asthmatic episode.

We have discovered and reported in parent application Ser. No. 08/516,786 that ultra-low molecular weight heparin (ULMWH) fractions are not only effective inhibitors of airway anaphylaxis, but are highly effective in reducing AHR even when administered after antigen challenge. Chronic, regular use of ULMWH may also reduce AHR, and ULMWH therefore may be used for chronic therapy of asthma whether caused by specific (i.e., antigenic) or non-specific factors.

Our prior application only pertained to, and disclosed test data demonstrating, the efficacy of ULMWH in the treatment of early phase asthma in acute responders, not in the treatment of "dual responders" who experience both early and late phase bronchoconstriction and prolonged AHR. As discussed previously, it could not have been predicted based on our earlier studies that ULMWH, whether administered before or after antigen challenge, would be efficacious in inhibiting bronchoconstriction (both early and late phase) and AHR in dual responders. This lack of predictability is evidenced by the fact that commercial heparin and medium or low molecular weight heparins (mol. wt. >3,000) inhibit AHR in acute responders when administered before antigen challenge, but have no significant effect in suppressing the late phase reaction and AHR observed in dual responders.

After conducting further controlled studies with ULMWH, we discovered, surprisingly, that heparin fractions having average molecular weights of about 1,000 to about 3,000 are effective, when inhaled by dual responders prior to or even after antigen challenge, in suppressing early and late phase bronchoconstriction and AHR.

Even more surprisingly, we found that oral and intravenous (or other parenteral) administration of ULMWH prior to antigen challenge effectively inhibited bronchoconstriction and AHR in dual responders.

Accordingly, the present invention comprises in one aspect a method of treating a mammalian patient who is a dual responder and suffers from antigen-induced late phase asthma comprising the intrabronchial administration to the patient before or after antigen challenge of a pharmaceutical composition containing about 0.005 to about 1.0 mg of one or more effective ULMWH fractions per kilogram of patient body weight in each dose of said composition, and preferably from about 0.075 to about 0.75 mg/kg per dose. For purposes of this application, the "effective ULMWH" may be defined as heparin fractions having an average molecular weight of about 1,000–3,000 daltons. ULMWH having an average molecular weight of about 1,000–2,500 daltons are particularly effective when used in the method of the invention. Each ULMWH fraction may comprise tetrasaccharides, pentasaccharides, hexasaccharides, septasaccharides, octasaccharides and decasaccharides as well as molecules of greater chain length.

The ULMWH fractions used in the invention are oligomers of sulfated saccharide units which may have, e.g., the following general structural formula:

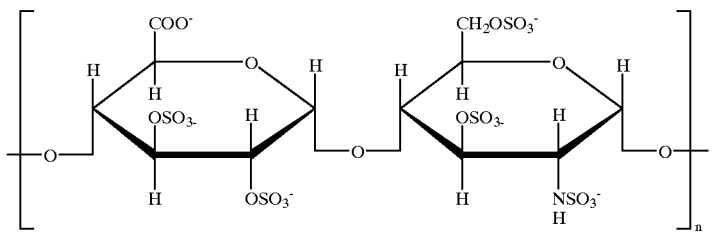

Despite the known activity of N-desulfated heparins in other biological systems, for example as inhibitors of cell growth, it has been found that the saccharide units in the ULMWH fractions which are effective for purposes of the present invention are all N-sulfated; N-desulfated fractions are ineffective.

While the sulfated polysaccharides used in the method and compositions of the invention are generally referred to herein as ultra-low molecular weight heparins, i.e., ultra-low molecular weight fractions derived from naturally occurring heparin (or synthetic versions of such ULMWH), the invention may also encompass the use of sulfated polysaccharides derived from heparan sulfate, dermatan sulfate, chondroitin sulfate, pentosan polysulfate and/or other glycosaminoglycans and mucopolysaccharides. The subject sulfated polysaccharide fractions must, however, have an average molecular weight of about 1,000–3,000 daltons. Pharmaceutically acceptable salts of the effective ULMWH or any of the other sulfated polysaccharides listed above may also be utilized, e.g., the sodium, calcium or potassium salts.

In accordance with this first aspect of the invention, a human or other mammalian patient who is a dual responder who has inhaled, ingested or otherwise come into contact with an antigen (i.e., has been "challenged" with an antigen) of a type known to provoke asthmatic episodes in that patient, or a patient who may be exposed at a future time to antigen challenge, is administered via inhalation at least one dose of a pharmaceutical composition containing one or more effective ULMWH cumulatively present in the above-described concentration ranges. Additional doses may subsequently be administered as necessary after antigen challenge until the patient regains or maintains normal airflow resistance levels.

The invention also comprehends in a second aspect the chronic administration of effective ULMWH to dual responder asthma patients to reduce and suppress early and late phase AHR. "Chronic administration" as used herein refers to administration of pharmaceutical compositions containing effective ULMWH at least once daily for at least ten consecutive days. Chronic administration of a composition containing from about 0.005–1.0 mg/kg per dose, and preferably about 0.0075–0.75 mg/kg per dose, can be continued indefinitely to provide AHR-suppressant therapy at least comparable to corticosteroids but substantially without side effects.

The inhalant (intrabronchial) ULMWH compositions used in the present invention to treat late phase asthma and other pulmonary conditions may comprise liquid or powder compositions containing effective ULMWH fractions and suitable for nebulization and intrabronchial use, or aerosol compositions administered via an aerosol unit dispensing metered doses.

Suitable liquid compositions comprise for example, effective ULMWH in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the mammalian patient's lungs.

Suitable powder compositions include, by way of illustration, powdered preparations of heparin thoroughly intermixed with lactose or other inert powders acceptable for intrabronchial administration. The powder compositions can be administered via an aerosol dispenser or encased in a breakable capsule which may be inserted by the mammalian patient into a device that punctures the capsule and blows the powder out in a steady stream suitable for inhalation.

Aerosol formulations for use in the subject method would typically include fluorinated alkane propellants, surfactants and co-solvents and may be filled into aluminum or other conventional aerosol containers which are then closed by a suitable metering valve and pressurized with propellant, producing a metered dose inhaler (MDI).

The total concentration of effective ULMWH in any propellant vehicle suitable for use in a pressured aerosol dispenser, such as an MDI, must be sufficiently high to provide a dose of about 0.005–0.1 mg (5–100 $\mu$g) of effective ULMWH per kilogram of patient body weight per administration. Thus, for example, if an MDI delivers about 85 $\mu$l of drug-containing propellant vehicle per actuation, the concentration of effective ULMWH in the vehicle in the case of a mammalian patient weighing 75 kg would be approximately 0.0045–0.088 mg/$\mu$l (4.5–88 $\mu$g/$\mu$l), delivering 0.375 to 7.5 mg (375–7,500 $\mu$g) of ULMWH per actuation, if it is desired to deliver the entire dose with a single actuation. If a two-actuation dose is desired, the corresponding concentration range would be approximately 0.0022–0.044 mg/$\mu$l (2.2–44 $\mu$g/$\mu$p), delivering 0.188 to 3.75 mg (188–3,750 $\mu$g) of ULMWH per actuation.

The total concentration of effective ULMWH in any liquid nebulizer solution must be sufficiently high to provide a dose of about 0.05–1.0 mg (50–1000 $\mu$g) of effective ULMWH per kilogram of patient body weight per administration. Thus, for example, if the nebulizer utilized delivers 5 ml of solution per actuation, the concentration of effective ULMWH in the case of a mammalian patient weighing 75 kg should be approximately 0.75–15.0 mg/ml.

In a further aspect of the invention, effective ULMWH-containing compositions are administered orally or parenterally (e.g., IV or IM) to mammalian patients suffering from antigen-induced late phase asthma, i.e., who are dual responders, prior to exposure of the patient to antigen-challenge. The oral or parenteral compositions contain about 0.005 to about 1.0 mg of effective ULMWH per kg of patient body weight in each dose. The oral or parenteral compositions may be administered up to 8 hours (but preferably not more than 4 hours) prior to antigen challenge and are effective in reducing early and late phase bronchoconstriction and in suppressing AHR.

As those skilled in the pharmaceutical arts will appreciate, many conventional methods and apparatus are available for administering precisely metered doses of intrabronchial medicaments and for regulating the desired dosage amount in accordance with patient weight and the severity of the patient's condition. Moreover, there are many art-recognized liquid, powder and aerosol vehicles suitable for the intrabronchial ULMWH compositions of the present invention, and many pharmaceutically acceptable oral and parenteral vehicles which may be employed for the oral and parenteral ULMWH-containing compositions. The invention is not limited to any particular inert vehicles, solvents, carriers excipients or dosage forms and is not restricted to any particular methods or apparatus of intrabronchial administration.

The pharmaceutical compositions may also be dosage forms which contain the effective ULMWH as active ingredients in any pharmaceutically acceptable oral, injectable or IV dosage vehicles, or in topical or intraocular vehicles. Each dosage form includes about 0.005–1.0 mg/kg of average patient body weight of effective ULMWH (one or a combination of ULMWH) and pharmaceutically acceptable inert ingredients, e.g., conventional excipients, vehicles, fillers, binders, disintegrants, solvents, solubilizing agents, sweeteners, coloring agents and any other inactive ingredients which are regularly included in pharmaceutical dosage forms for oral administration. Suitable oral dosage forms include tablets, capsules, caplets, gelcaps, pills, liquid solutions, suspensions or elixirs, powders, lozenges, micronized particles and osmotic delivery systems. Injectable and IV dosage forms include isotonic saline solutions or dextrose solutions containing suitable buffers and preservatives. Many suitable dosage forms and vehicles, and listings of inactive ingredients therefor, are well-known in the art and are set forth in standard texts such as *Remington's Pharmaceutical Sciences,* 17th edition (1985).

The ULMWH compositions described herein provide highly effective treatment for early and late phase antigen-induced asthma even after antigen challenge has occurred, as well as for other conditions characterized by late phase allergic reactions.

To demonstrate the unexpected superiority of the effective ULMWH in comparison with higher molecular weight heparins in treating asthmatic dual responders, experiments were conducted comparing the effects of different heparin types on dual responder allergic sheep, both before and after antigen challenge. Detailed descriptions of these experiments and of the results obtained are set forth in the following examples as well as in the graphs shown in the drawings.

The following examples, while illustrating the methods and compositions of the invention and demonstrating the efficacy of the same, are not intended to set forth specific compositions, materials, procedures or dosage regimens which must be utilized exclusively in order to practice the invention.

EXAMPLE 1

Administration of Inhaled ULMWH to Dual Responder Allergic Sheep

Methods

Pulmonary Airflow Resistance:

Allergic sheep with previously documented dual bronchoconstrictor response to *Ascaris suum* antigen were used for all studies. The sheep were intubated with a cuffed nasotracheal tube and pulmonary airflow resistance ($R_1$) was measured by the esophageal balloon catheter technique, while thoracic gas volume was measured by body plethysmography. Data were expressed as specific $R_L$ ($SR_L$, defined as $R_L$ times thoracic gas volume ($V_{tg}$)).

Airway Responsiveness:

To assess airway responsiveness, cumulative dose-response curves to inhaled cabachol were performed by measuring $SR_L$ before and after inhalation of buffered saline and after each administration of 10 breaths of increasing concentrations of carbachol (0.25, 0.5, 1.0, 2.0 and 4.0% wt/vol solution). Airway responsiveness was measured by determining the cumulative provocation dose ($PD_{400}$) of carbachol (in breath units) that increased $SR_L$ to 400% above baseline. One breath unit was defined as one breath of 1% carbachol solution.

Heparin Fractions:

In the studies reported herein various heparin materials were administered to the dual responder allergic sheep prior to and/or after antigen challenge. Some of these heparins were ULMWH fractions of average molecular weight between 1,000 and 3,000 daltons, some were of higher average molecular weight, and one was of lower molecular weight. The heparin fractions tested are set forth in Table 1 below.

TABLE 1

HEPARIN FRACTIONS AND THEIR MOLECULAR WEIGHTS

| FRACTION | AVG. MOL. WT. | CATEGORY |
|---|---|---|
| Commercial heparin | 15,000 d | Heparin |
| Fragmin ™ | 5,030 d | Low mol. wt. |
| CY-216 | 4,270 d | Low mol. wt. |
| CY-222[1] (Sanofi) | 2,355 d | ULMWH |
| FRU-70[2] (Kabivitrum) | 2,500 d | ULMWH |
| Hexasaccharide mixture[3] | 1,930 d | ULMWH |
| Octasaccharide[4] | 2,480 d | ULMWH |
| Purified hexasaccharide[5] | 1,998 d | ULMWH |
| Purified tetrasaccharide[6] | 1,290 d | ULMWH |
| Disaccharide[7] | 660 d | Sub-ULMWH |

[1]An anticoagulant octasaccharide mixture.
[2]A non-anticoagulant octasaccharide mixture.
[3]Oligosaccharide derived from commercial porcine heparin, comprising primarily tetrasaccharide, hexasaccharide, octasaccharide and decasaccharide fractions.
[4]Obtained from the hexasaccharide mixture by gel column chromatography, comprises about 70% octasaccharide and 30% decasaccharide fractions.
[5]Obtained from the hexasaccharide mixture by gel column chromatography.
[6]Obtained from the hexasaccharide mixture by gel column chromatography.
[7]The disaccharide was trisulfated but had a molecular weight so low it could not be considered a ULMWH fraction with heparin-like properties.

Experimental Protocol

Airway Studies

Each animal's baseline airway responsiveness ($PD_{400}$) was determined, and then on different experimental days the sheep underwent airway challenge with *Ascaris suum* antigen. $SR_L$ was measured, before and immediately after challenge, and then hourly for 8 hours. The post-challenge $PD_{400}$ was measured 24 hours after antigen challenge when AHR occurred. The protocol was repeated at least 14 days later, but each animal was administered a dose of one of the test heparin fractions either about 30 minutes before antigen challenge or immediately after post-challenge $SR_L$ measurement.

Data Analysis

Data were expressed as:

$$SR_L \text{ (\% change)} = \frac{\text{post challenge } SR_L - \text{baseline } SR_L \times 100}{\text{baseline } SR_L} \quad \text{(a)}$$

$$PD_{400} \text{ (in breath units)} \quad \text{(b)}$$

Results

Figure 1:
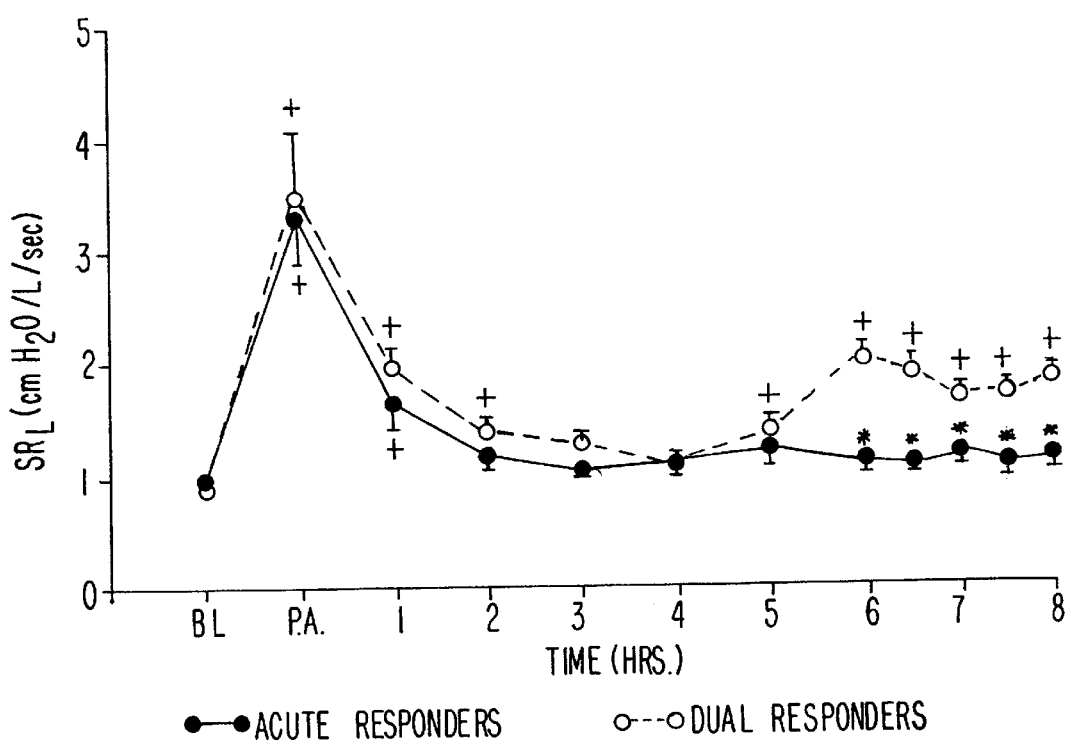
FIG. 1 is a graph illustrating the effects of antigen challenge on two groups of allergic sheep, one composed of acute responders and the other of dual responders. Data for each group are shown as antigen-induced mean ±SE% change in $SR_L$ (specific lung resistance), shown before (baseline), immediately after (P.A.) and up to 8 hours post-antigen.

FIG. 1 illustrates the differential reactions to antigen challenge of two groups of allergic sheep, one composed of acute responders and the other of dual responders. The $SR_L$ of the acute responders returned to approximately baseline levels after about three hours post-antigen and remained there. In the dual responders, however, there is a late phase peak in $SR_L$ at about six hours with levels remaining significantly above baseline through the eight-hour end point of the study. It is this second, late phase peak which characterizes dual responders.

Figure 2A:
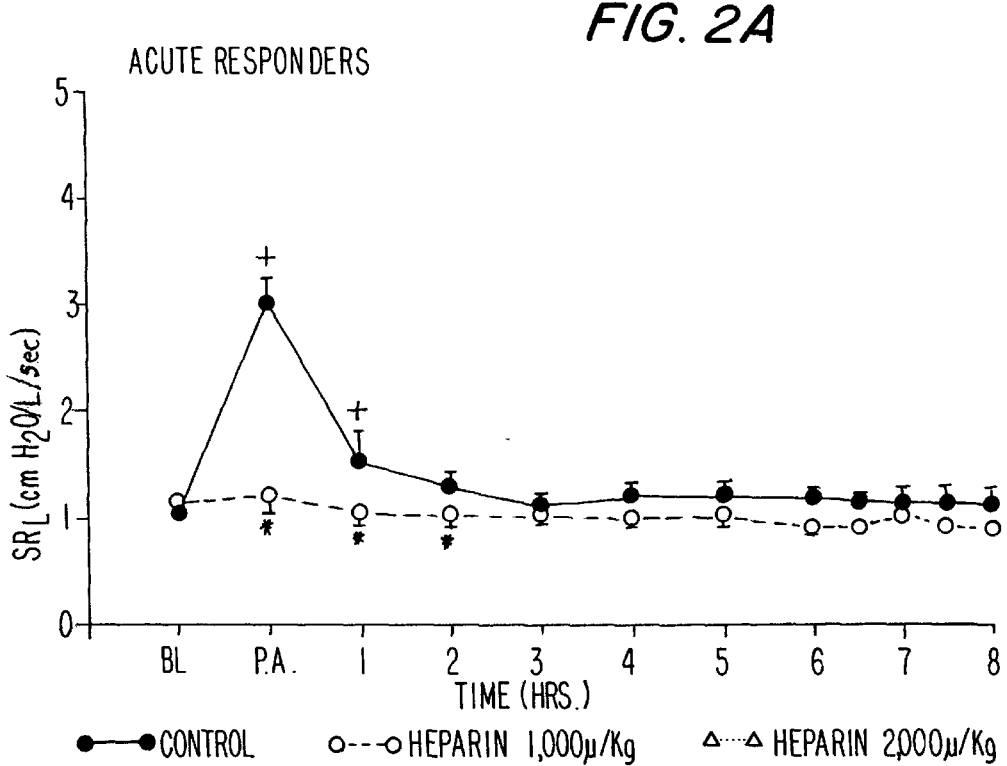
Figure 2B:
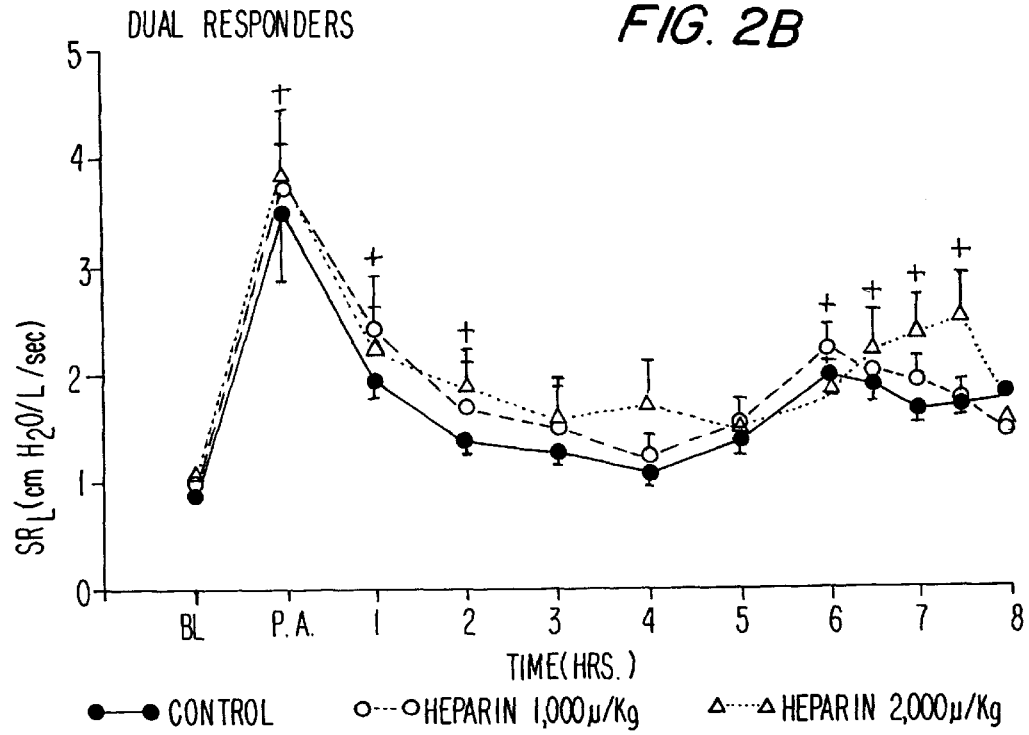

FIGS. 2A and 2B depict the effects of pre-challenge treatment with inhaled commercial heparin on $SR_L$ in acute responders (FIG. 2A) and in dual responders (FIG. 2B). While the $SR_L$ of the acute responders remained at near-baseline levels even after antigen challenge, both the early phase and the late phase $SR_L$ in the dual responders was not alleviated by heparin pretreatment, even in dual responders administered as much as 2000 units per kilogram.

FIGS. 3–6 illustrate the lack of efficacy of the low molecular weight heparin fractions, Fragmin and CY-216, in modifying either bronchoconstriction or AHR in dual responders when administered prior to antigen challenge.

FIGS. 7–10 show that both pretreatment and post-antigen challenge treatment with the inhaled ULMWH CY-222 (avg. mol. wt. 2355 d, within the range of effective ULMWH in accordance with the invention) were effective in significantly modifying both early and late phase antigen-induced bronchoconstriction and AHR in the dual responders.

FIGS. 11–14 illustrate the efficacy of both pretreatment and post-antigen challenge treatment with the ULMWH FRU-70 (avg. mol. wt. 2500 d) in the treatment of early and late phase asthma.

FIGS. 15–22 demonstrate the efficacy of various effective ULMWH fractions, even when administered post-antigen challenge, in significantly reducing bronchoconstriction and AHR in dual responders.

FIG. 23 shows that the disaccharide fraction, having an average molecular weight of only about 660 d (substantially below the weight range required for the effective ULMWH fractions) was ineffective in modifying antigen-induced bronchoconstriction in the dual responder allergic sheep.

In the experiments whose data are reflected in FIGS. 7–14 and 17–22 the dosage of the effective ULMWH administered to the allergic sheep was the lowest effective dose (determined through dose-ranging trials) for each ULMWH fraction. It will be observed that the different ULMWH had varying minimum effective dose levels in the treatment of dual responders. The minimum effective dose was about 1.0 mg/kg for CY-222 and for FRU-70 administered prior to antigen challenge, but about 0.5 mg/kg for FRU-70 administered post-antigen challenge and for the inhaled hexasaccharide mixture. The purified tetrasaccharide, having the lowest average molecular weight of any of the effective ULMWH tested, had a minimum effective dose when administered post-antigen of 0.062 mg/kg, as did the purified hexasaccharide. These data tend to suggest that purified fractions having an average weight near the lower limit of about 1,000 d may be the most effective ULMWH, at least in the treatment of dual responders. The optimal structural domain and/or sequence for the observed antiallergic and/or anti-inflammatory activity appears to be the tetrasaccharide.

EXAMPLE 2

Administration of Oral ULMWH to Dual Responder Allergic Sheep

The procedure of Example 1, in terms of the test animals and evaluation methods, were followed in the present experiment.

One dual-responder allergic sheep was administered orally 2 mg/kg of purified hexasaccharide (avg. mol. wt. 1998 daltons) 90 minutes before challenge with *Ascaris Suum* antigen. The effects of the pretreatment with the hexasaccharide on $SR_L$ from baseline (time of administration of the hexasaccharide) through 8 hours after antigen challenge is reflected on FIG. 24. Also shown on FIG. 24 for comparison purposes is the percentage change in $SR_L$ in the same dual responder sheep (in an experiment conducted several days earlier) challenged with antigen but without ULMWH pretreatment.

Shown in FIG. 25 are the respective $PD_{400}$ values measured at baseline and post-antigen when the sheep was administered antigen challenge with hexasaccharide pretreatment and with no pretreatment (control).

EXAMPLE 3

Administration of Intravenous ULMWH to Dual Responder Allergic Sheep

The procedure of Example 2 was followed with another dual responder allergic sheep, except that 0.25 mg/kg of purified hexasaccharide was administered intravenously one hour before antigen challenge in one experiment, while antigen was administered with no pretreatment in the second (control) experiment. The percentage change in $SR_L$ for the pretreatment and control experiments are shown in FIG. 26 and the $PD_{400}$ values for those experiments at baseline and post-antigen are shown in FIG. 27.

EXAMPLE 4

Prevention of Antigen-induced Eosinophil Influx in Mice

In four groups of sensitized laboratory mice (n=3 in each group) bronchoalveolar lavage was performed 24 hours after antigen challenge to determine eosinophil influx values in each group. The mice were treated with either aerosolized saline (placebo) or purified hexasaccharide administered by the following routes and in the following dosage amounts, respectively: inhaled aerosol,[8] oral (100 μg) and intraperitoneal (40 μg). The percentage inhibition of eosinophil influx effected in each treatment group was determined by comparing the level of such influx measured in bronchoalveolar ravage fluid subsequent to hexasaccharide administration with the saline group.

The mean percentage inhibition values for the three treatment groups of mice are reflected in FIG. 28. The mice receiving inhaled and oral hexasaccharide showed a 40–50% reduction in eosinophil influx while the mice receiving intraperitoneal hexasaccharide showed about a 20% reduction in such influx.

[8]The mice (n=3) were placed in a chamber containing 10 mg of hexasaccharide in 9 ml of bacteriostatic injection water, which was aerosolized. The mice were allowed to inhale the aerosol for about 30 minutes.

The differential effects of commercial heparin observed in acute and dual responders (shown in FIGS. 2A and 2B) might indicate the involvement of different signaling pathways during airway anaphylaxis. This would suggest that during immunologically mediated mast-cell reaction in the airways, $IP_3$ is the predominantly active pathway in "acute responders" while non-$IP_3$ pathways (e.g., diacylglycerol/protein kinase C or other pathways) may be operative in "dual responders".

The late phase response and AHR are associated with marked airway inflammation. The pathological studies of the airway mucosa and bronchoalveolar lavage (BAL) have shown influx of eosinophils, neutrophils and activated T-lymphocytes during this phase. Increased levels of eosinophil-derived inflammatory mediators in plasma and BAL, including eosinophilic cationic protein and major basic protein, have been observed during the late phase reaction. Upregulation of $TH_2$-type cytokines ($IL_4$ and $IL_5$) following allergen challenge has also been observed during the late phase. Thus, the cellular inflammatory response, in combination with released pro-inflammatory mediators (e.g., leukotrienes, PAF, eosinophilic proteins, etc.) and locally produced cytokines in the bronchial mucosa, play a central role in the late phase allergic inflammation and bronchoconstriction.

AHR and thus airway inflammation can be modified either by prevention of mast mediator release by "antiallergic agents" (e.g., cromolyn sodium) or by the action of "anti-inflammatory" agents like glucocorticosteroids. The "anti-allergic" agents are only effective as prophylactic agents and can prevent the mediator release and AHR. Because these agents do not possess anti-inflammatory activity, they are generally ineffective when administered after the exposure to antigen. By contrast "antiinflammatory" agents can attenuate post-antigen AHR and airway inflammation, whether administered before or after the exposure to antigen. Our data suggest that the actions of ULMWH are analogous to the anti-inflammatory actions of glucocorticosteroids.

Since the effective ULMWH can modify AHR even when administered after antigen challenge, they should also be useful in the treatment of non-asthmatic conditions associated with AHR, e.g., chronic bronchitis, emphysema and cystic fibrosis.

Moreover, in view of our findings regarding the efficacy of certain ULMWH in inhibiting asthmatic LPR in a manner resembling the anti-inflammatory effects of corticosteroids, the effective ULMWH should be useful in the treatment of the following conditions and by the following routes of administration:

1. Late phase reactions and inflammatory response in extra-pulmonary sites:

(a) allergic rhinitis (b) allergic dermatitis (c) allergic conjunctivitis

2. Extra-pulmonary diseases where inflammatory response plays a major role:
(I) inflammatory bowel disease
(ii) rheumatoid arthritis and other collagen vascular diseases
(iii) glomerulonephritis
(iv) inflammatory skin diseases
(v) sarcoidosis
3. Routes of Administration
(I) intrabronchial
(ii) intranasal
(iii) intraocular
(iv) topical
(v) oral
(vi) parenteral (IM or IV)

It should be emphasized, however, that the invention is not restricted or limited in any way to any theoretical or actual physiological or biochemical mechanisms or pathways, but comprehends the methods of treatment of conditions characterized by late phase allergic reactions, or treatment of dual responder mammalian patients, and the compositions for use in said methods described hereinabove, notwithstanding the actual mechanisms of action involved.

It has thus been shown that there have been provided methods and compositions which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by letters patent is set forth in the following claims.

I claim:

1. A method of treating a mammalian patient suffering from or prone to a condition whose symptoms include late phase allergic reactions, airway hyperresponsiveness or inflammatory reactions, said method comprising the administration to the patient of a pharmaceutical composition containing about 0.005 to about 1.0 mg of ultra-low molecular weight heparins (ULMWH) per kilogram of patient body weight in each dose, said ULMWH having an average molecular weight of about 1,000 to about 3,000 daltons.

2. A method according to claim 1 wherein said ULMWH have an average molecular weight of about 1,000 to about 2,500 daltons.

3. A method according to claim 1 wherein said ULMWH comprise heparin fractions selected from the group consisting of tetrasaccharides, pentasaccharides, hexasaccharides, septasaccharides, octasaccharides and decasaccharides and pharmaceutically acceptable salts thereof.

4. A method according to claim 1 wherein said ULMWH are N-sulfated.

5. A method according to claim 1 wherein said composition contains about 0.075 to about 0.75 mg of said ULMWH per kilogram per dose.

6. A method according to claim 1 wherein said ULMWH are non-anticoagulant.

7. A method according to claim 1 wherein said composition is administered by the oral, parenteral, topical, intrabronchial, intranasal or intraocular routes.

8. A method according to claim 7 wherein said parenteral administration is intravenous or intramuscular.

9. A method according to claim 1 wherein said symptoms are late phase allergic reactions selected from the group consisting of pulmonary late phase reactions, nasal late phase reactions, cutaneous late phase reactions, ocular late phase reactions and systemic late phase reactions.

10. A method according to claim 9 wherein said late phase reactions are pulmonary late phase reactions.

11. A method according to claim 10 wherein said condition is late phase asthma.

12. A method according to claim 1 wherein said condition is a non-asthmatic condition characterized by airway hyperresponsiveness.

13. A method according to claim 12 wherein said condition is selected from the group consisting of chronic bronchitis, emphysema and cystic fibrosis.

14. A method according to claim 1 wherein said symptoms are inflammatory reactions.

15. A method according to claim 1 wherein said condition is selected from the group consisting of allergic rhinitis, allergic dermatitis, allergic conjunctivitis, inflammatory bowel disease, rheumatoid arthritis, collagen vascular diseases, glomerulonephritis, inflammatory skin diseases and sarcoidosis.

16. A method according to claim 1 wherein said composition comprises a solution or suspension of said ULMWH in an aqueous, pharmaceutically acceptable, liquid inhalant vehicle.

17. A method according to claim 16 wherein said vehicle is isotonic saline or bacteriostatic water.

18. A method according to claim 16 wherein said composition is administered by means of a pump or squeeze-actuated nebulizer.

19. A method according to claim 16 wherein a sufficient amount of said composition is administered to the patient to provide a dose of about 0.05–1.0 mg/kg of said ULMWH.

20. A method according to claim 16 wherein said composition contains about 0.75–15.0 mg/ml of said ULMWH.

21. A method according to claim 1 wherein said composition is an aerosol composition comprising an aerosol propellant.

22. A method according to claim 21 wherein said composition is dispensed via a metered dose inhaler.

23. A method according to claim 21 wherein a sufficient amount of said composition is administered to the patient to provide a dose of about 0.005–0.1 mg/kg of said ULMWH.

24. A method according to claim 21 wherein said composition contains about 2.2–88 $\mu g/\mu l$ of said ULMWH.

25. A method according to claim 1 wherein said composition comprises a powdered preparation of said ULMWH intermixed with an inert powder acceptable for intrabronchial administration.

26. A method according to claim 25 wherein said inert powder is lactose.

27. A method according to claim 25 wherein said composition is administered via an aerosol dispenser.

28. A method according to claim 25 wherein said composition is administered from a breakable capsule.

29. A method according claim 1 wherein said composition is administered to the patient prior to challenge with allergic reaction-inducing antigen.

30. A method according claim 1 wherein said composition is administered to the patient subsequent to challenge with allergic reaction-inducing antigen.

31. A method of treating a mammalian patient suffering from or prone to a condition whose symptoms include late phase allergic reactions, airway hyperresponsiveness or inflammatory reactions, said method comprising the administration to the patient of a pharmaceutical composition containing about 0.005 to about 1.0 mg of sulfated polysaccharides per kilogram of patient body weight in each dose, said sulfated polysaccharides having an average molecular weight of about 1,000 to about 3,000 daltons.

32. A method according to claim 31 wherein said sulfated polysaccharides are derived from glycosaminoglycans or mucopolysaccharides.

33. A method according to claim 32 wherein said sulfated polysaccharides are derived from heparin, heparan sulfate, dermatan sulfate, chondroitin sulfate or pentosan polysulfate.

34. A method according to claim 31 wherein said sulfated polysaccharides comprise tetrasaccharides, pentasaccharides, hexasaccharides, septasaccharides, octasaccharides and decasaccharides and pharmaceutically acceptable salts thereof.

35. A method according to claim 34 wherein said sulfated polysaccharides comprise tetrasaccharides.

* * * * *